United States Patent [19]

Karasawa et al.

[11] Patent Number: 5,798,422

[45] Date of Patent: Aug. 25, 1998

[54] AROMATIC HYDROXYCARBOXYLIC ACID RESINS AND THEIR USE

[75] Inventors: Akio Karasawa; Akihiro Yamaguchi, both of Kanagawa-ken; Keizaburo Yamaguchi, Chiba-ken; Yuko Ishihara, Kanagawa-ken, all of Japan

[73] Assignee: Mitsui Toatsu Chemicals, Inc., Tokyo, Japan

[21] Appl. No.: 511,809

[22] Filed: Aug. 7, 1995

[30] Foreign Application Priority Data

| Aug. 25, 1994 | [JP] | Japan | 6-200836 |
| Aug. 25, 1994 | [JP] | Japan | 6-200837 |
| Aug. 25, 1994 | [JP] | Japan | 6-200838 |
| Oct. 13, 1994 | [JP] | Japan | 6-247883 |

[51] Int. Cl.$^6$ .................. C08G 61/02; C08F 6/02; C08F 6/00
[52] U.S. Cl. ............................. 525/450; 528/206
[58] Field of Search ...................... 528/206; 525/450

[56] References Cited

FOREIGN PATENT DOCUMENTS

| 61-141441 | 6/1986 | Japan. |
| 62-164716 | 7/1987 | Japan. |
| 62-176875 | 8/1987 | Japan. |
| 64-44439 | 2/1989 | Japan. |
| 1-77032 | 7/1989 | Japan. |
| 1-280748 | 11/1989 | Japan. |
| 2-10350 | 1/1990 | Japan. |
| 1571487 | 7/1980 | United Kingdom. |

OTHER PUBLICATIONS

Journal of Organic Chemistry, "Polymeric Ligands. I. Some Salicyclic Acid Derivatives", vol. 27, pp. 1424–1426, 1962.
Patel et al. "Friedel–Crafts Polymers . . . ", J. Macromol. Sci., Chem. (1986), A23(10), 1251–61.

*Primary Examiner*—Jeffrey Mullis
*Attorney, Agent, or Firm*—Burns, Doane, Swecker & Mathis

[57] ABSTRACT

Disclosed are an aromatic hydroxycarboxylic acid resin represented by the following formula (1):

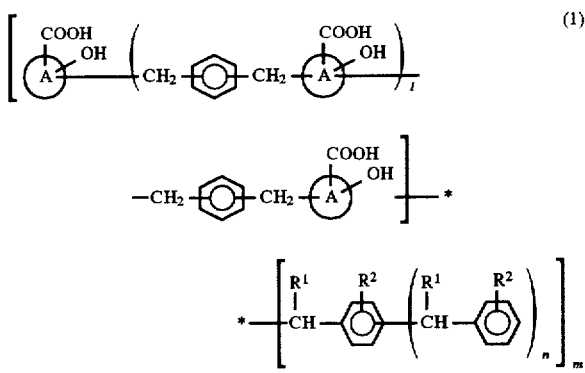

wherein each A group is the same or different and individually represents a substituted or unsubstituted phenylene or naphthylene group, $R^1$ represents a hydrogen atom or a $C_{1-4}$ alkyl group, $R^2$ represents a hydrogen atom or a $C_{1-10}$ alkyl, $C_{1-10}$ alkoxyl, nitro or hydroxyl group, l stands for an integer of 0–100, m stands for an integer of 0–20 and n stands for an integer of 0–3 with the proviso that m stands for an integer other than 0 when all of the A group represent an unsubstituted or substituted a group, a preparation process thereof and use of the same.

11 Claims, 8 Drawing Sheets

AROMATIC HYDROXYCARBOXYLIC ACID RESINS AND THEIR USE

BACKGROUND OF THE INVENTION a. Field of the Invention

This invention relates to a novel hydroxycarboxylic acid resin, and also to its production process and use. The hydroxycarboxylic acid resin according to the present invention is useful inter alia as a photoresist resin composition with excellent sensitivity and resolving power, as a metal chelate resin with excellent flexibility, oxidation resistance and waterproofness, as a color-developing agent for pressure-sensitive copying paper or an intermediate therefor, and as an epoxy resin curing agent.

b. Description of the Related Art

As photoresist resins, phenol or cresol novolak resins are used in general. A composition formed of a diazidonaphthoquinonesulfonate and a novolak resin is used as a positive resist, because when exposed to light of 300–500 nm, quinone diazide groups are decomposed into carboxyl groups and the diazidonaphthoquinonesulfonate is hence converted from the alkaline-solution-insoluble form into an alkaline-solution-soluble form. This positive resist features far superior resolving power to negative resists and is used for the fabrication of integrated circuits such as ICs and LSIs. With respect to integrated circuits, miniaturization has progressed in recent years, keeping step with the high densification, so that formation of patterns on the order of submicrons is now demanded. As a result, still better resolving power is required even for positive resists. In the case of a resist material formed of a diazidonaphthoquinonesulfonate and a novolak resin, there is a limitation to the improvement of the resolving power as long as conventional available materials are combined. An improvement in resolving power might be contemplated, for example, by increasing the content of the quinone diazide compound. An increase in the content of the quinone diazide compound however is accompanied by serious drawbacks such as a reduction in sensitivity and an increase in development residue. There is hence a limitation to the improvement of the resolving power, resulting in the demand for a base resin as a substitute for phenol or cresol novolak resins.

There have also been attempts to improve the sensitivity and developability of a resist composition by adding a specific compound thereto. For example, Japanese Patent Laid-Open No. 141441/1986 discloses a positive composition containing trihydroxybenzophenone. A problem with this trihydroxybenzophenone-containing positive photoresist however is that the heat resistance is deteriorated by the addition of trihydroxybenzophenone, although the sensitivity and developability have been improved. Further, Japanese Patent Laid-Open Nos. 44439/1989, 177032/1989, 280748/1989 and 10350/1990 disclose techniques for increasing the sensitivity without reducing the heat resistance by the addition of aromatic polyhydroxy compounds other than trihydroxybenzophenone. However, these techniques are not considered to be sufficient with respect to the improvement of developability.

On the other hand, salicylic acid novolak resins have already been known as metal chelate resins, cement dispersants, metal coating thickeners, fiber treatments, color-developing materials for pressure-sensitive copying paper, and the like. Resins of this type are each produced by reacting salicylic acid with formaldehyde in the presence of an acid catalyst [for example, Journal of Organic Chemistry (J. Org. Chem.), 27, 1424(1962); publications in which the former publication is referred to.]. Further, Japanese Patent Laid-Open Nos. 164716/1987 and 176875/1987 disclose novel salicylic acid resins, i.e., xylok resins. Like novolak resins represented by phenol-formaldehyde resin, however, salicylic acid novolak resins are accompanied by such drawbacks as low flexibility and susceptibility to oxidation and deterioration. To meet the high physical properties required in recent years, there is increasing recognition that improvements to the resins themselves are indispensable. Further, the salicylic-acid-base xylok resins are accompanied by the drawback that they have low waterproofness.

SUMMARY OF THE INVENTION

An object of the present invention is to provide a photoresist composition having high resolving power and high sensitivity as are required upon fabrication of highly integrated circuits. Another object of the present invention is to provide a novel hydroxycarboxylic acid resin which exhibits excellent performance in flexibility, oxidation resistance, formability, workability and the like and is useful as a metal chelate resin, a color-developing agent for pressure-sensitivity copying paper or an intermediate therefor, an epoxy resin curing agent, and the like, and also a production process thereof.

With a view to overcoming the above-described problems, the present inventors have proceeded with an extensive investigation. As a result, aromatic hydroxycarboxylic acid resins according to the present invention have been invented.

Described specifically, the present invention relates to an aromatic hydroxycarboxylic acid resin represented by the following formula (1):

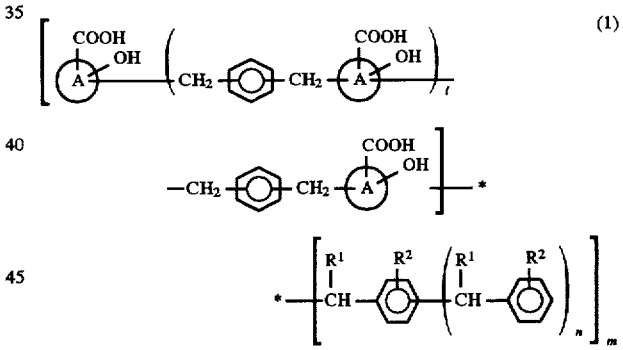

wherein each A group is the same or different and individually represents a substituted or unsubstituted phenylene or naphthylene group, $R^1$ represents a hydrogen atom or a $C_{1-4}$ alkyl group, $R^2$ represents a hydrogen atom or a $C_{1-10}$ alkyl, $C_{1-10}$ alkoxyl, nitro or hydroxyl group, l stands for an integer of 0–100, m stands for an integer of 0–20 and n stands for an integer of 0–3 with the proviso that m stands for an integer other than 0 when all of the A groups represent a phenyl group.

In the formula (1),

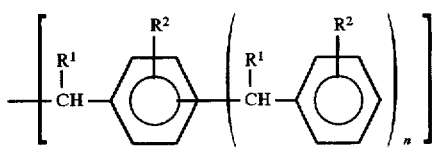

groups are substituted on at least one ring of the rings A in

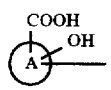

and/or the benzene rings in

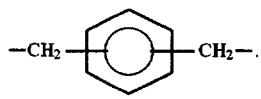

This applies equally to other formulas which will be shown hereinafter.

The present invention also relates to an aralkylated salicylic acid resin represented by the formula (2); an aralkylated hydroxynaphthoic acid resin represented by the formula (3); a hydroxynaphthoic acid represented by the formula (4); a hydroxynaphthoic acid co-condensation resin obtained by reacting hydroxynaphthoic acid represented by the formula (5), a hydroxybenzoic acid represented by the formula (6) and a xylylene compound represented by the formula (7); a process for the production of a hydroxynaphthoic acid resin, which comprises reacting the hydrooxynaphthoic acid represented by the formula (5) and the xylylene compound represented by the formula (7); and a process for the production of the aralkylated resin, which comprises reacting a resin represented by the formula (8) or (10) with an aralkyl compound represented by the formula (9).

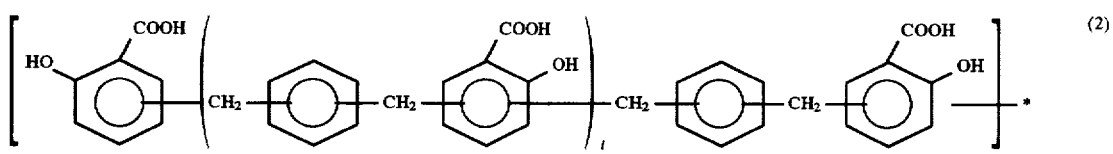 (2)

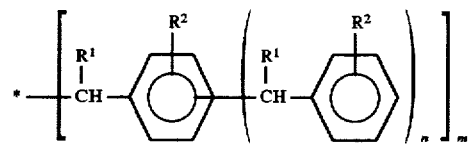

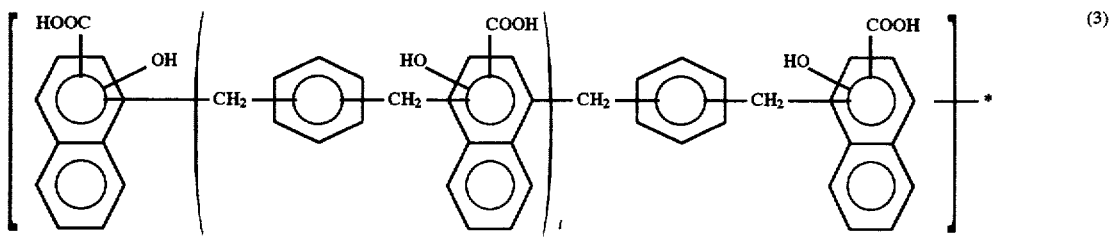 (3)

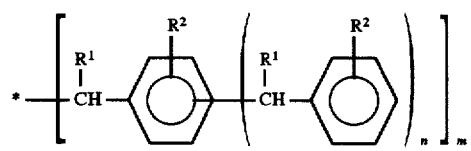

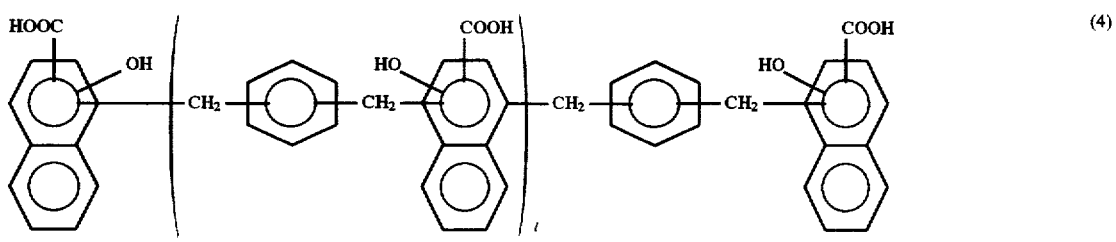 (4)

 (5)

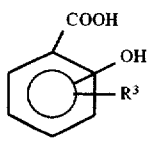
(6)

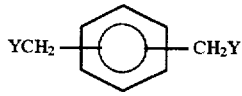
(7)

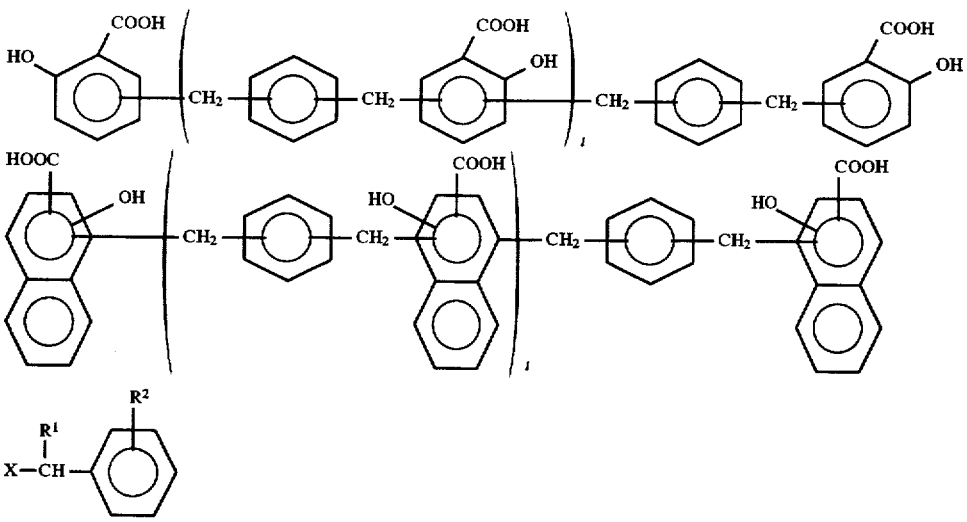
(8)

(10)

(9)

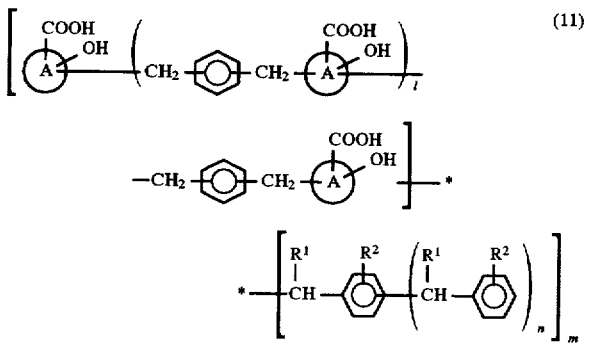

wherein R¹ represents a hydrogen atom or a $C_{1-4}$ alkyl group, R² represents a hydrogen atom or a $C_{1-10}$ alkyl, $C_{1-10}$ alkoxyl, nitro or hydroxyl group, R³ represents a hydrogen atom or a $C_{1-10}$ alkyl group, X represents a halogen atom, Y represents a halogen atom or a hydroxyl or $C_{1-4}$ alkoxyl group, l stands for an integer of 0–100, m stands for an integer of 1–20, and n stands for an integer of 0–3.

In addition, the present invention also relates to a partial esterification product of a hydroxycarboxylic acid resin represented by the formula (11); a photoresist composition comprising the hydroxycarboxylic acid resin represented by the formula (11) or the partial esterification product thereof; a multivalent-metal-modified product of the hydroxycarboxylic acid resin represented by the formula (1); and a color-developing sheet comprising the multi-valent-metal-modified product.

$$\left[\begin{array}{c}\text{COOH}\\ \text{OH}\\ \text{A}\end{array}\left(\text{CH}_2-\bigcirc-\text{CH}_2-\text{A}\begin{array}{c}\text{COOH}\\ \text{OH}\end{array}\right)_l\right.$$

$$\left.-\text{CH}_2-\bigcirc-\text{CH}_2-\text{A}\begin{array}{c}\text{COOH}\\ \text{OH}\end{array}\right]_*$$

$$*\left[\begin{array}{cc}R^1 & R^2\\ | & |\\ \text{CH}-\bigcirc & \end{array}\left(\begin{array}{cc}R^1 & R^2\\ | & |\\ \text{CH}-\bigcirc\end{array}\right)_n\right]_m$$

wherein each A group is the same or different and individually represents a substituted or unsubstitued phenylene or naphthlylene group, R¹ represents a hydrogen atom or a $C_{1-4}$ alkyl group, R² represents a hydrogen atom or a $C_{1-10}$ alkyl, $C_{1-10}$ alkoxyl, nitro or hydroxyl group, l stands for an integer of 0–100, m stands for an integer of 0–20, and n stands for an integer of 0–3.

These resins are useful as photoresist resins excellent in sensitivity and resolving power, metal chelate resins excellent in flexibility, oxidation resistance and waterproofness, and color-developing materials for pressure-sensitive copying paper or intermediates therefor. Due to their structures, they can also be usd as curing agents for epoxy resins.

DETAILED DESCRIPTION OF THE INVENTION AND PREFERRED EMBODIMENTS

Figure 1:
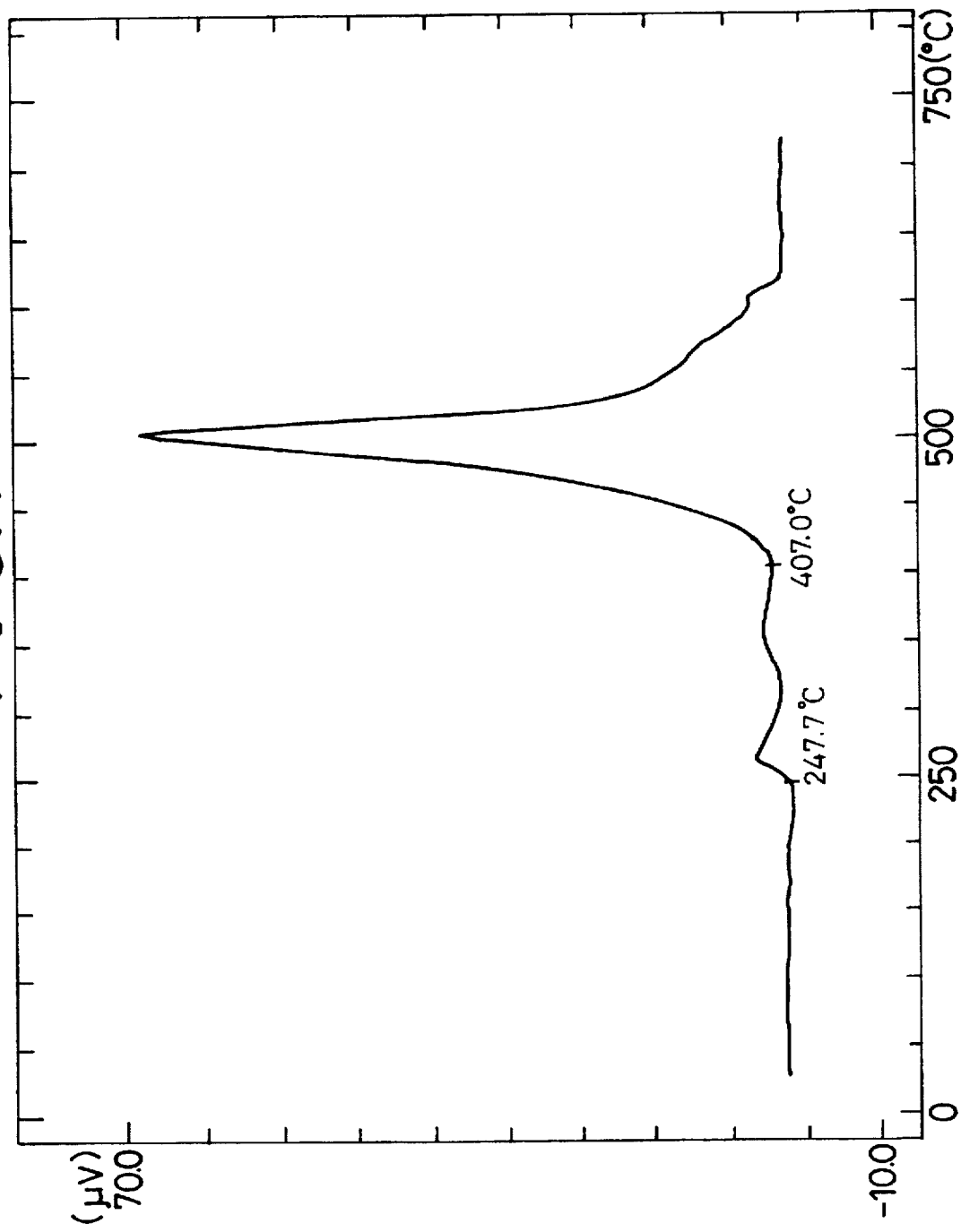
FIG. 1 diagrammatically shows the results of a DTA analysis of the resin obtained in Synthesis Example 1.

The term "aromatic hydroxycarboxylic acid resin" as used herein means a hydroxycarboxylic acid resin according to the present invention is obtained by reacting a hydroxycarboxylic acid represented by the formula (12) and the xylylene derivative represented by formula (7) and also an aralkylated hydroxycarboxylic acid resin obtained by further reacting the hydroxycarboxylic acid resin with the aralkyl compound represented by the formula (9).

wherein A represents a substituted or unsubstituted phenyl or naphthyl group.

Examples of the hydroxycarboxylic acid represented by the formula (12) include substituted or unsubstituted 2-hydroxybenzoic acid, 3-hydroxybenzoic acid and 4-hydroxybenzoic acid when A represents a phenyl group. When A represents a naphthyl group, examples include substituted or unsubstituted 1-hydroxy-2-naphtoic acid, 2-hydroxy-1-naphthoic acid, 2-hydroxy-3-naphthoic acid, 2-hydroxy-6-naphthoic acid, 1-hydroxy-4-naphthoic acid, 1-hydroxy-5-naphthoic acid, 2-hydroxy-7-naphthoic acid and 1-hydroxy-8-naphthoic acid.

Illustrative substituents include alkyl groups such as methyl, ethyl, propyl, isopropyl, butyl, isobutyl, pentyl and octyl; halogenated alkyl groups such as trifluoromethyl, trifluoroethyl, hexafluorobutyl and hexafluorononyl; alkoxyl groups such as methoxy, ethoxy, propoxy, butoxy and pentyloxy; halogen atoms such as fluorine, chlorine, iodine and bromine; hydroxyl; nitro; and cyano. Instead of the hydroxycarboxylic acid represented by the formula (12), its esters can also be used in the present invention.

Examples of the xylylene derivative represented by the formula (7) include α,α'-dihydroxy-o-xylene, α,α'-dihydroxy-m-xylene, α,α'-dihydroxy-p-xylene, α,α'-dimethoxy-m-xylene, α,α'-dimethoxy-p-xylene, α,α'-diethoxy-o-xylene, α,α'-diethoxy-p-xylene, α,α'-diethoxy-m-xylene, α,α'-diisopropoxy-o-xylene, α,α'-diisopropoxy-m-xylene, α,α'-diisopropoxy-p-xylene, α,α'-di-n-propoxy-p-xylene, α,α'-di-n-butoxy-m-xylene, α,α'-di-n-butoxy-p-xylene, α,α'-di-sec-butoxy-p-xylene, α,α'-diisobutyl-p-xylene, α,α'-dichloro-o-xylene, α,α'-dichloro-m-xylene, α,α'-dichloro-p-xylene, α,α'-dibromo-o-xylene, α,α'-dibromo-m-xylene, α,α'-dibromo-p-xylene, α,α'-difluoro-o-xylene, α,α'-difluoro-m-xylene, α,α'-difluoro-p-xylene, α,α'-diiodo-o-xylene, α,α'-diiodo-m-xylene, and α,α'-diiodo-p-xylene. Preferred compounds are α,α'-dihydroxy-p-xylene, α,α'-dichloro-p-xylene, α,α'-dimethoxy-p-xylene, α,α'-dihydroxy-m-xylene, α,α'-dichloro-m-xylene, α,α'-dimethoxy-m-xylene, and the like.

Examples of the aralkyl compound represented by the formula (9) include benzyl chloride, benzyl bromide, 3-methylbenzyl chloride, 4-methylbenzyl bromide, 4-methoxybenzyl bromide, 2-methoxybenzyl chloride, 3-ethoxybenzyl chloride, 2-nitrobenzyl bromide, 4-nitrobenzyl bromide, 3-hydroxybenzyl bromide, α-chloroethylbenzene, and α-bromoethylbenzene.

In the production of each hydroxycarboxylic acid resin (m=0) of aromatic hydroxycarboxylic acids represented by the formula (1) of the invention, the reaction between the corresponding hydroxycarboxylic acid and the corresponding xylylene derivative is conducted in a catalystless manner or in the presence of an acid catalyst by using the xylylene derivative in an amount of 0.1–1.0 mole per mole of the hydroxycarboxylic acid. The reaction temperature can be 50°–250° C. while the reaction time can be 1–20 hours.

The acid catalyst can be either an inorganic acid or an organic acid. Exemplary inorganic acids include mineral acids such as hydrochloric acid, phosphoric acid and sulfuric acid; and Friedel-Crafts catalysts such as zinc chloride, stannic chloride and ferric chloride. Illustrative organic acids include organic sulfonic acids such as methanesulfonic acid, trifluoromethanesulfonic acid and p-toluenesulfonic acid. These catalysts can be used either singly or in combination. The catalyst can be used in an amount of from about 0.01 to 15 wt. % based on the total weight of the hydroxycarboxylic acid of the formula (12) and the xylylene derivative of the formula (7).

In the reaction of the present invention, a solvent can be used. Usable exemplary solvents include halogenated hydrocarbons such as dichloroethane, trichloroethane, chlorobenzene and dichlorobenzene; ethers such as diethylene glycol dimethyl ether, diethylene glycol diethyl ether, dipropylene glycol dimethyl ether and tetrahydrofuran; and sulfur-containing solvents such as sulfolane and dimethylsulfoxide.

Further, each aralkylated hydroxycarboxylic acid resin (m≠0) of aromatic hydroxycarboxylic acids represented by the formula (1) of the invention can be obtained by reacting the corresponding aralkyl compound represented by the formula (9) to the corresponding hydroxycarboxylic acid resin obtained above. The aralkyl compound represented by the formula (9) can be used at a weight ratio of 0.1–10, preferably 0.1–1 relative to the hydroxycarboxylic acid resin obtained above. The reaction can be conducted in a catalystless manner or in the presence of an acid catalyst at 50°–250° C. for 1–20 hours.

As the acid catalyst, any one of the above-exemplified acid catalysts is usable. It can be used in an amount of about 0.01–15 parts by weight per 100 parts by weight of the total weight of the hydroxycarboxylic acid resin and the aralkyl compound of the formula (9). Further, a solvent can be used for the reaction. Usable examples of the solvent include nitrogen-containing solvents such as dimethylformamide, N-methylpyrrolidone, N,N-dimethylformamide, N,N-dimethylacetamide and dimethylimidazolidinone, to say nothing of the solvents exemplified above.

When a reaction is conducted using a hydroxycarboxylate ester instead of the hydroxycarboxylic acid, it is necessary to hydrolyze the resulting carboxylic acid resin with an alkali such as sodium hydroxide or potassium hydroxide into the corresponding carboxylic acid either after condensation or after aralkylation.

The partially esterified hydroxycarboxylic acid resin from the hydroxycarboxylic acid resin represented by the formula (11) that some of the carboxylic groups have been esterified, can be obtained by partially esterifying the hydroxycarboxylic acid resin, which has been obtained as described above, with a known esterifier.

This partial esterification reaction can be conducted by reacting the hydroxycarboxylic acid resin and the esterifier in the presence of an alkali in an organic solvent at 50°–150° C. for 1–20 hours while using the esterifier in an amount of 0.1–70 mole %, preferably 1–50 mole % per mole of each carboxyl group in the hydroxycarboxylic acid resin. Illustrative usable esterifiers include alkyl halides such as methyl iodide, ethyl iodide, butyl iodide, methyl bromide, ethyl bromide, methyl chloride and butyl chloride; sulfate esters such as dimethyl sulfate and diethyl sulfate; and p-toluenesulfonate esters.

Illustrative usable alkalis include carbonates such as sodium carbonate and potassium carbonate; hydrogencarbonates such as sodium hydrogencarbonate and potassium hydrogencarbonate; oxides such as magnesium oxide and silver oxide; and hydroxides such as sodium hydroxide and potassium hydroxide.

As the organic solvent employed upon conducting the reaction, any one of the above-described various solvents including the nitrogen-containing solvents can be used.

A description will hereinafter be made of the manner of use of the resin according to the present invention for the formulation of a photoresist composition.

The photoresist composition comprises the aromatic hydroxycarboxylic acid resin of the present invention represented by the formula (11) and/or a partially estrified resin thereof, another alkaline-solution-soluble resin, a diazidonaphthoquinonesulfonate and a solvent. Additives such as other resins, dyes, sensitivity modifiers and the like can also be added in small amounts as needed.

The proportion of the resin according to this invention in the whole alkaline-solution-soluble resins may range from 0.1 to 100 wt. %, preferably from 0.5 to 50 wt. %, more preferably from 1 to 30 wt. %.

Preferred resins among the resins according to the present invention include aralkylated salicylic acid resins represented by formula (2) and having a number average molecular weight of 450–20000, more preferably 500–7000 and a carboxylic acid equivalent of 245–440 g/eq; aralkylated hydroxynaphthoic acid resins represented by the formula (3) and having a number average molecular weight of 510–20000, more preferably 520–7000 and a carboxylic acid equivalent of 232–400 g/eq; hydroxynaphthoic acid resins represented by the formula (4) and having a number average molecular weight of 500–50000, more preferably 550–7000 and a carboxylic acid equivalent of 240–288 g/eq; co-condensation resins of hydroxynaphthoic acid and hydroxybenzoic acid, which have a number average molecular weight of 370–50000, preferably 400–7000; and esterification products obtained by esterifying 1–50 mole % of the carboxyl groups in the preferred resins exemplified above. Most preferred are aralkylated salicylic acid resins represented by the formula (2) in which l, m and n are 0–10, 1–10 and 0–3; hydroxynaphthoic acid resins represented by the formula (4) in which the hydroxyl group and the carboxyl group in each benzene ring are at ortho position to each other and l is 0–10; and resins obtained by esterifying 1–50 mole % of the carboxyl groups in these most preferred resins.

Where these resins are used as photoresist compositions, it is preferred for the resins to have high solubility in a solvent. Solubility of 2% or higher, preferably 10% or higher in a solvent is needed. From this standpoint, the partial esterification products have higher solubility than their corresponding resins before the esterification and are therefore preferred. Incidentally, the other properties of the partial esterifiation products are similar to the corresponding properties of their corresponding resins before the esterification.

Other alkaline-solution-soluble resins include, for example, so-called novolak resins obtained by condensing phenols and/or naphthols with aldehydes, such as novolak, cresol novolak and naphthol novolak; copolymers between phenols and/or naphthols and dicyclopentadiene; polyhydroxystyrene and its hydride; styrene-maleic anhydride copolymer; and poly(methyl methacrylate).

Any diazidonaphthoquinonesulfonate can be used in the present invention insofar as it has been derived from a phenolic compound. Illustrative examples include 1,2-diazidonaphthoquinone-4-sulfonate and 1,2-diazidonaphthoquinone-5-sulfonate derived from hydroquinone; resorcin; phloroglucin; hydroxybenzophenones such as 2,4-dihydroxybenzophenone, 2,3,4-trihydroxybenzophenone, 2,3,3',4-tetrahydroxybenzophenone, 2,3,4,4'-tetrahydroxybenzophenone, 2,2',3,3'-tetrahydroxybenzophenone, 2,2',3,3',4'-pentahydroxybenzophenone and 2,3,3',4,5'-pentahydroxybenzophenone; alkyl gallates; bis((poly)hydroxyphenyl)alkanes such as 2,2-bis((poly)hydroxyphenyl)alkanes and 2-(3-hydroxyphenyl)-2-(2,5-dihydroxyphenyl)propane; and hydroxyflavanes.

The diazidonaphthoquinonesulfonate component may preferably amount to 10–50 wt. % of the whole solids in the composition.

Preferred as the solvent is one capable of providing the photoresist composition with an adequate drying rate and permitting formation of a uniform smooth coating subsequent to its evaporation. Examples of such solvents include ethylene glycol monomethyl ether, ethylene glycol monoethyl ether, Ethyl Cellosolve acetate, Methyl Cellosolve acetate, diethylene glycol monoethyl ether, propylene glycol monopropyl ether acetate, toluene, xylene, propylene glycol, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl piruvate, methyl 3-methoxypropionate, ethyl 3-methoxypropionate, methyl 3-ethoxypropionate, ethyl 3-ethoxypropionate, butyl acetate, ethyl lactate, methyl isobutyl ketone, cyclohexanone, 2-heptanone, 3-heptanone, and 4-heptanone. These solvents can be used either singly or in combination.

In the photoresist composition according to the present invention, it is preferred to control the solid concentration within 20–40 wt. %.

The composition so formulated may preferably be filtered to eliminate any insoluble matter. The composition is then coated on a substrate such as a silicon wafer on a spin coater. The thus-coated silicon wafer is next baked at 50°–150° C. for 30–180 seconds. Through a photomask, this wafer is imagewise exposed on an aligner. The coating so exposed is then developed with an aqueous alkaline solution, whereby a pattern is obtained.

As the aqueous alkaline solution, it is possible to use an aqueous alkaline solution obtained by dissolving, generally to a concentration of 1–10 wt. %, preferably 2–5 wt. %, an alkaline compound such as sodium hydroxide, potassium hydroxide, sodium carbonate, ammonia (in the form of aqueous ammonia), ethylamine, n-propylamine, diethylamine, di-n-propylamine, triethylamine, methyldiethylamine, dimethylethanolamine, tetramethylammonium hydroxide, choline, piperidine, 1,8-diazabicyclo-(5,4,0)-7-undecene or the like.

As radiation to be employed upon exposure, ultraviolet rays such as i-rays are preferred. However, various radiations can be selectively used depending on the properties and the like of the composition.

The high sensitivity and high resolving power of the photoresist composition containing the hydroxycarboxylic acid according to the present invention may presumably be attributed to hydrogen bonding between the naphthoquinone diazide as a photosensitizer and the hydroxycarboxylic acid so that the difference in the solubility of the resin in an aqueous alkaline solution before and after its exposure to light is widened.

A description will next be made of the manner of production of a multivalent-metal-modified product of the aromatic hydroxycarboxylic acid resin of this invention represented by the formula (1) and also of the manner of its use as a color-developing agent for pressure-sensitive copying paper.

To produce a multivalent-metal-modified product from each resin according to the present invention, a conventionally-known process can be applied. For example, it can be produced by reacting an alkali metal salt of the resin with a water-soluble multivalent metal salt in water or a solvent in which the alkali metal salt and the multivalent metal salt are both soluble. Described specifically, this is a process in which the hydroxide, the carbonate, an alkoxide or the like of an alkali metal is reacted with the resin to obtain the alkali metal salt of the resin or an aqueous solution, alcohol solution or water-alcohol mixed solution thereof and the water-soluble multivalent metal salt is reacted to form the multivalent-metal-modified product of the resin. The water-soluble multivalent metal salt is desirably reacted in an amount of about 0.5–1 gram equivalent per mole of carboxyl groups in the resin.

The multivalent-metal-modified product can also be produced by mixing the resin of the present invention with a multivalent metal salt of an organic carboxylic acid such as formic acid, acetic acid, propionic acid, valeric acid, caproic acid, stearic acid or benzoic acid and then heating and melting the resultant mixture. In some instances, a basic substance, for example, ammonium carbonate, ammonium hydrogencarbonate, ammonium acetate or ammonium benzoate is added further, and the mixture so obtained is heated, melted and reacted.

As a still further alternative, the resin according to the present invention and the carbonate, oxide or hydroxide of the multivalent metal are used. They are heated and melted together with a basic substance such as an organic ammonium carboxylate, e.g., ammonium formate, ammonium acetate, ammonium caproate, ammonium stearate or ammonium benzoate, whereby a reaction is conducted. The reaction product is then cooled to obtain the multivalent-metal-modified product.

Upon production of the multivalent-metal-modified product of the resin according to the present invention by heating and melting, the melting temperature can generally be 100°–180° C. and the reaction time can be 1 to several hours or so although the reaction time varies depending on the resin composition, the melting temperature, and the kind and amount of the multivalent metal salt. Regarding the multivalent metal salt, it is desired to use an organic carboxylate salt, the car- bonate, oxide or hydroxide of the multivalent metal so that the multivalent metal is present in an amount of 1 wt. % to about 20 wt. % based on the total weight of the resin.

Although no particular limitation is imposed on the amount of the basic substance to be used, the basic substance is used generally in an amount of 1–15 wt. % based on the whole resin. When the basic substance is used, it is more preferable to use it after mixing it with a multivalent metal salt in advance.

Illustrative examples of the metal in the multivalent-metal-modified product of the resin according to the present invention include metals other than alkali metals such as lithium, sodium and potassium. Preferred exemplary multivalent metals include calcium, magnesium, aluminum, copper, zinc, tin, barium, cobalt and nickel, with zinc being more preferred.

The color-developing sheet according to the present invention can be produced inter alia by any one of the following methods:

(1) To coat a base material such as paper with a water-base coating composition which makes use of an aqueous suspension of the multivalent-metal-modified resin.

(2) To incorporate the multivalent-metal-modified resin upon making paper.

(3) To coat a base material with an oil-base coating composition in which the multivalent-metal-modified resin is dissolved or suspended in an organic solvent.

Upon formulation of these coating compositions, a clay such as kaolin, calcium carbonate, starch, a synthetic or natural latex and/or the like are added to provide the coating compositions with an appropriate viscosity and coating applicability. In each of these coating compositions, the multivalent-metal-modified resin may desirably amount to 10–70 wt. % of the whole solids. Proportions smaller than 10 wt. % cannot exhibit sufficient color developability whereas proportions greater than 70 wt. % tend to result in color-developing sheets with reduced paper surface properties.

Further, each of the coating compositions is applied in an amount sufficient to give a dry coat weight of at least 0.5 g/m$^2$, preferably 1–10 g/m$^2$.

The present invention will hereinafter be described more specifically by Examples, in which all designations of "part" or "parts" and "%" mean part or parts by weight and wt. % unless otherwise specifically indicated. It should however be borne in mind that this invention is by no means limited to or by the examples.

SYNTHESIS EXAMPLE 1

In a reactor equipped with a thermometer and a stirrer, 913 parts of methyl salicylate and 0.2 part of trifluoromethanesulfonic acid were charged, followed by heating to 140°–150° C. To the resulting mixture, 498 parts of α,α'-dimethoxy-p-xylene were added dropwise at the same temperature over 5 hours. The reaction mixture was subjected to aging at 150° C. for 2 hours. The pressure was reduced to 10 mmHg by a pump and unreacted methyl salicylate was separated for reuse at 150°–180° C. After the reaction mixture was allowed to cool down to 100° C., 350 ml of toluene were added, whereby a toluene solution of a salicylate resin was obtained. In a reactor equipped with a thermometer and a stirrer, 160 parts of caustic soda and 907 parts of water were charged, followed by the dropwise addition of the above-obtained toluene solution at 85°–90° C. over 4 hours. The temperature was then raised to 100° C. and the toluene was distilled off.

After removal of insoluble matter, the residue was neutralized with 2,250 parts of an 8% aqueous solution of hydrochloric acid. The solid so precipitated was collected by filtration, washed with water and then dried. The yield was 720 parts.

Figure 2:
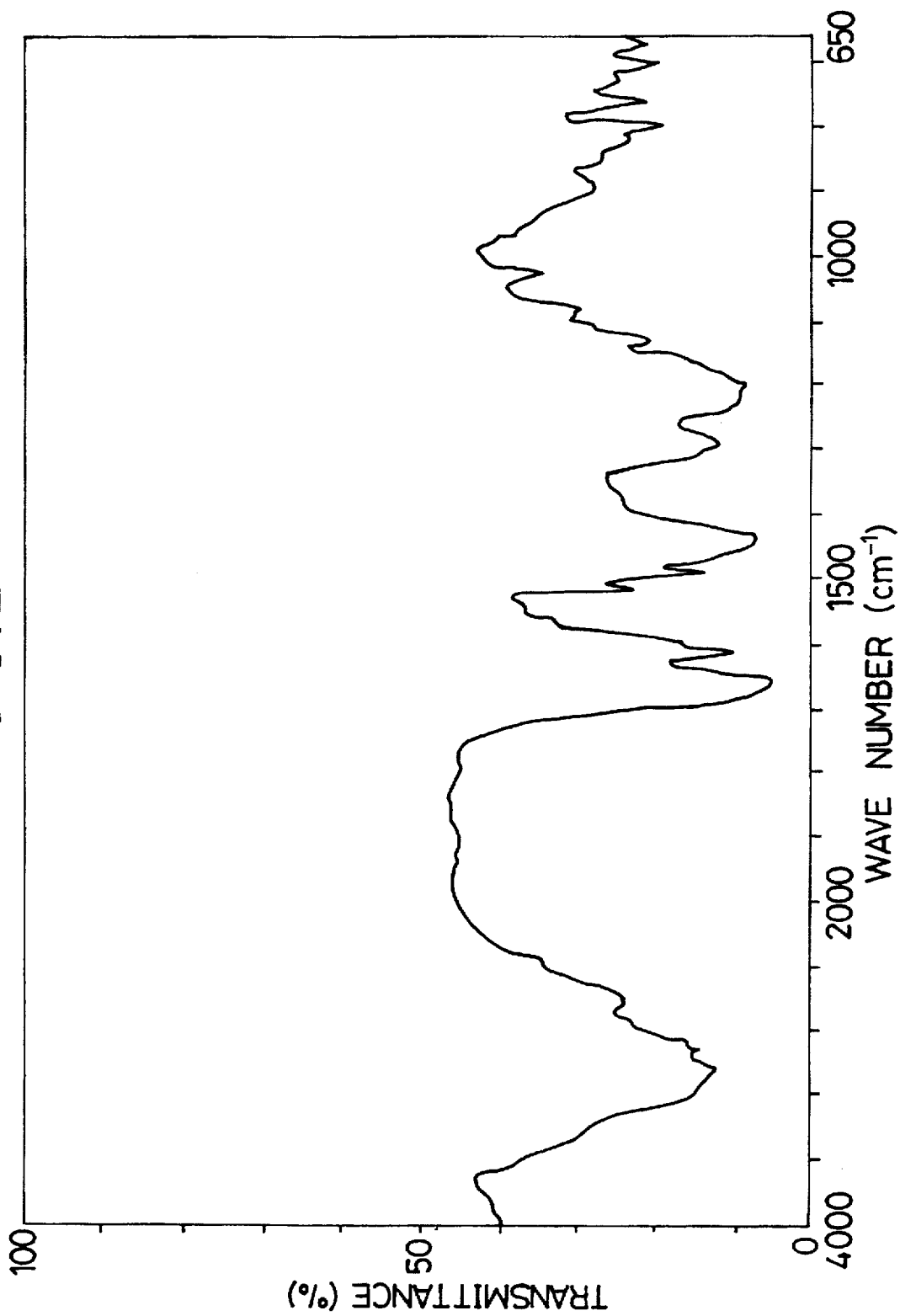
FIG. 2 diagrammatically illustrates the results of an IR analysis of the resin obtained in Synthesis Example 1.

In a reactor equipped with a thermometer and a stirrer, 100 parts of the above-obtained salicylic acid resin [composition (area %) according to a GPC analysis: 50.4% l=0, 23.6% l=1, 1.5% l=2, 4.0% l≧3 and 0.5% others, number-average molecular weight: 533], 33.5 parts of benzyl chloride, 400 parts of 1,1,2-trichloroethane and 0.4 part of zinc chloride, followed by reaction at 110° C. for 3 hours. After completion of the reaction, 1,000 parts of water were added and the 1,1,2-trichloroethane was distilled off azeotropically. The solid so precipitated was collected by filtration and dried, whereby 121 parts of an aralkylated salicylic acid resin were obtained. The resin was found to have a number-average molecular weight of 632 and a carboxylic acid equivalent of 249 g/eq. The results of a DTA analysis and IR analysis (according to the KBr tablet method) of the resin are shown in FIGS. 1 and 2, respectively.

Incidentally, the carboxylic acid equivalent was determined at room temperature by titration of a 0.1N methanol solution of potassium hydroxide while using cresol red as an indicator.

SYNTHESIS EXAMPLE 2

Figure 3:
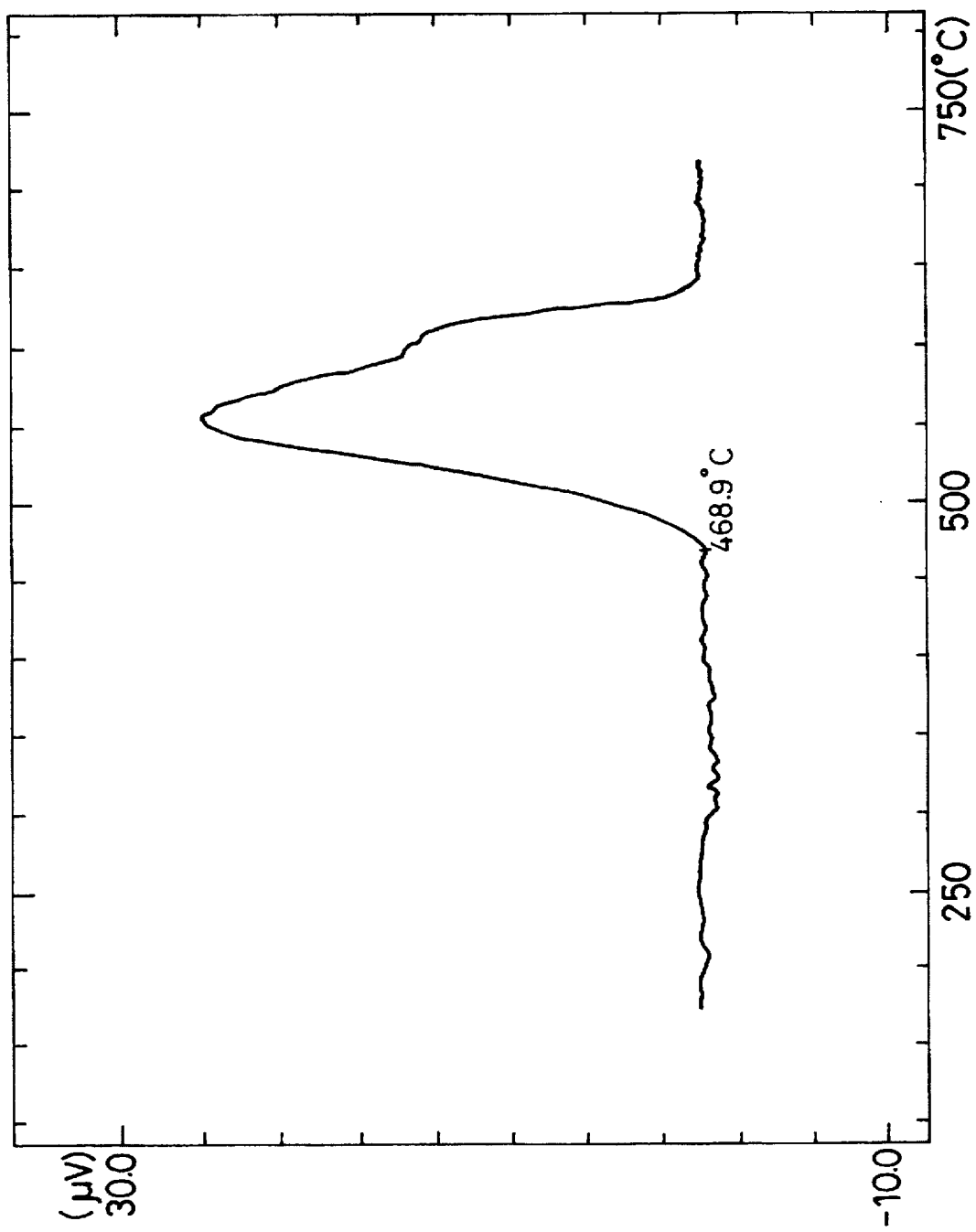
FIG. 3 diagrammatically shows the results of a DTA analysis of the resin obtained in Synthesis Example 2.
Figure 4:
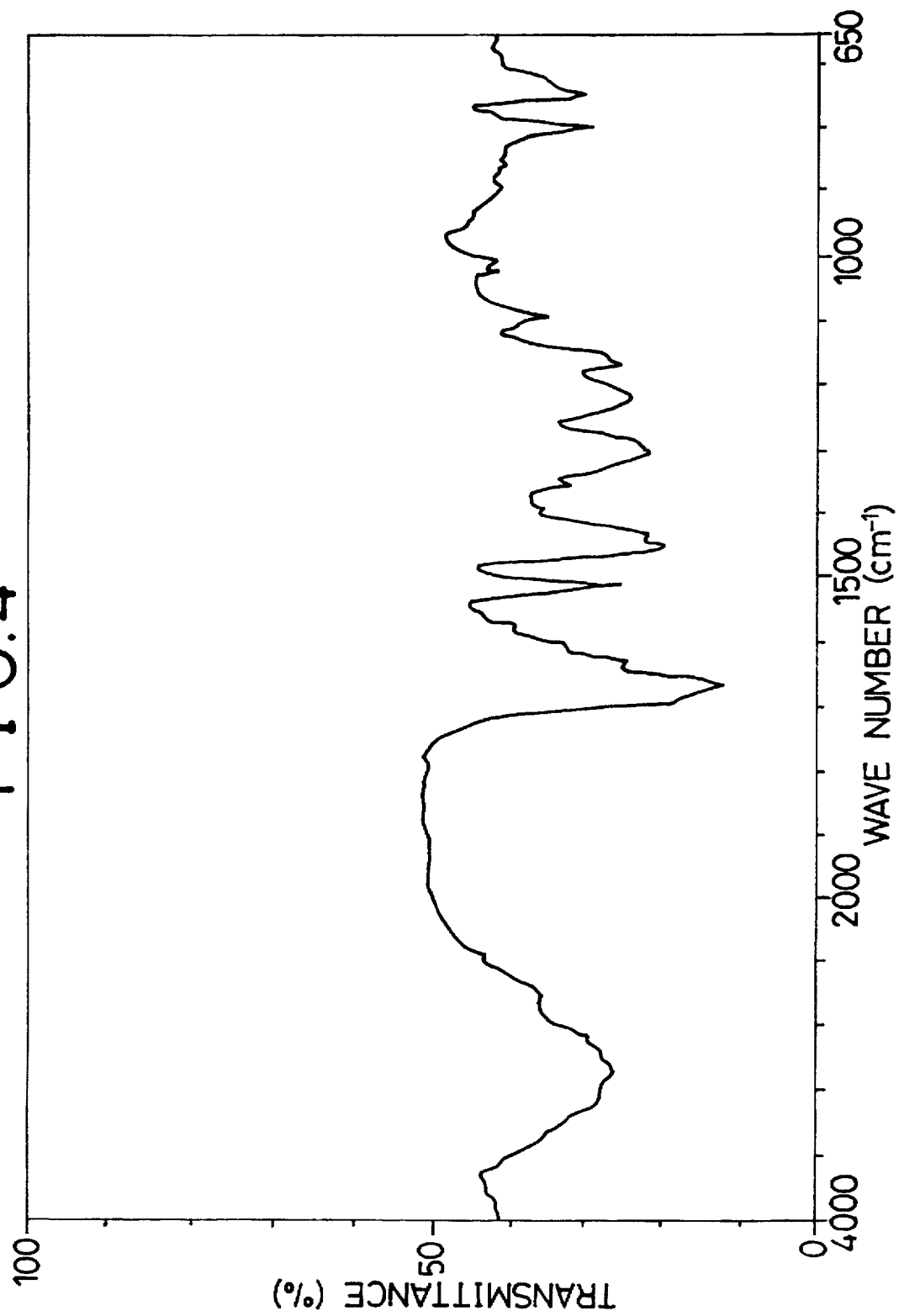
FIG. 4 diagrammatically illustrates the results of an IR analysis of the resin obtained in Synthesis Example 2.

In a reactor equipped with a thermometer and a stirrer, 200 parts of 2-hydroxy-3-naphthoic acid, 200 parts of sulfolane and as a catalyst, 0.06 part of trifluoromethanesulfonic acid were charged, followed by the dropwise addition of 58.9 parts of α,α'-dimethoxy-p-xylene over 5 hours at 140°–150° C. The reaction was continued further for 2 hours at 150° C. The reaction mixture was then poured into 1,000 parts of water. The solid so precipitated was collected by filtration and then dried. The resulting solid was added to 1,500 parts of toluene, followed by heating and stirring. Thermal filtration was then repeated three times to remove unreacted raw materials, whereby 154 parts of a purified resin were obtained. In accordance with an analysis by GPC, the resulting resin was found to have the following composition (area %): 53.2% l=0, 31.2% l=1, 13.5% l≧2 and 2.1% others and also have a carboxylic acid equivalent of 250 g/eq and a number-average molecular weight of 673. The results of a DTA analysis and IR analysis (according to the KBr tablet method) of the resin are shown in FIGS. 3 and 4, respectively.

SYNTHESIS EXAMPLE 3

In a reactor equipped with a thermometer and a stirrer, 100 parts of the hydroxynaphthoic acid resin, which had been obtained in Synthesis Example 2, 0.4 part of zinc chloride and 300 parts of sulfolane were charged, followed by heating to 100° C. To the resulting mixture, 40.8 parts of benzyl chloride were added dropwise over one hour at the same temperature. The reaction mixture was stirred under heat at 120° C. for 5 hours, at 130° C. for 2 hours and then at 140° C. for 3 hours. After allowed to cool down, the reaction mixture was poured into 1,500 parts of water and the solid so precipitated was collected by decantation. The solid so obtained was added to 1,500 parts of water to form a sludge and the remaining sulfolane was removed. The solid was collected by filtration, washed with water and dried, whereby 90 parts of an aralkylated hydroxynaphthoic acid resin were obtained.

Figure 5:
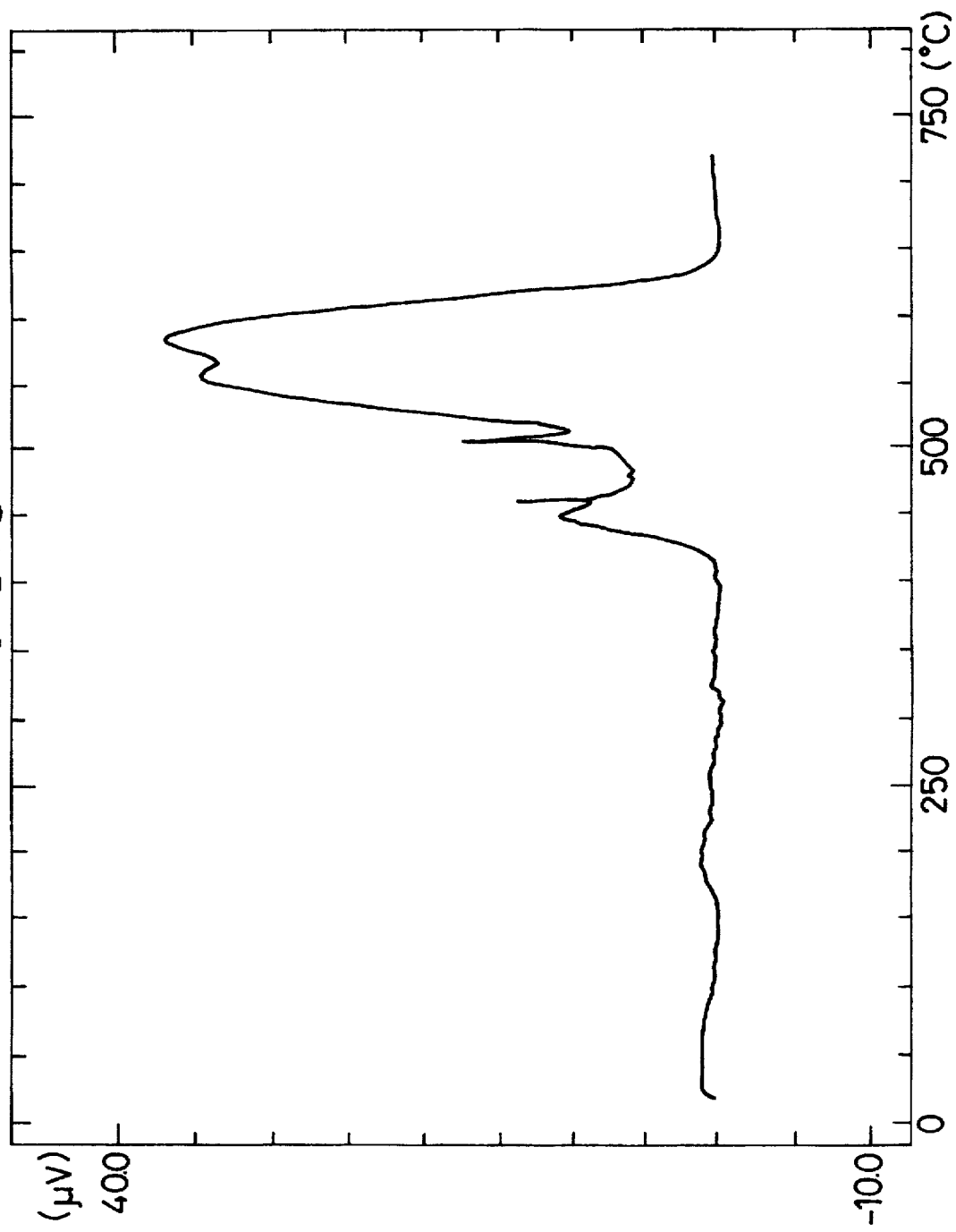
FIG. 5 diagrammatically shows the results of a DTA analysis of the resin obtained in Synthesis Example 3.
Figure 6:
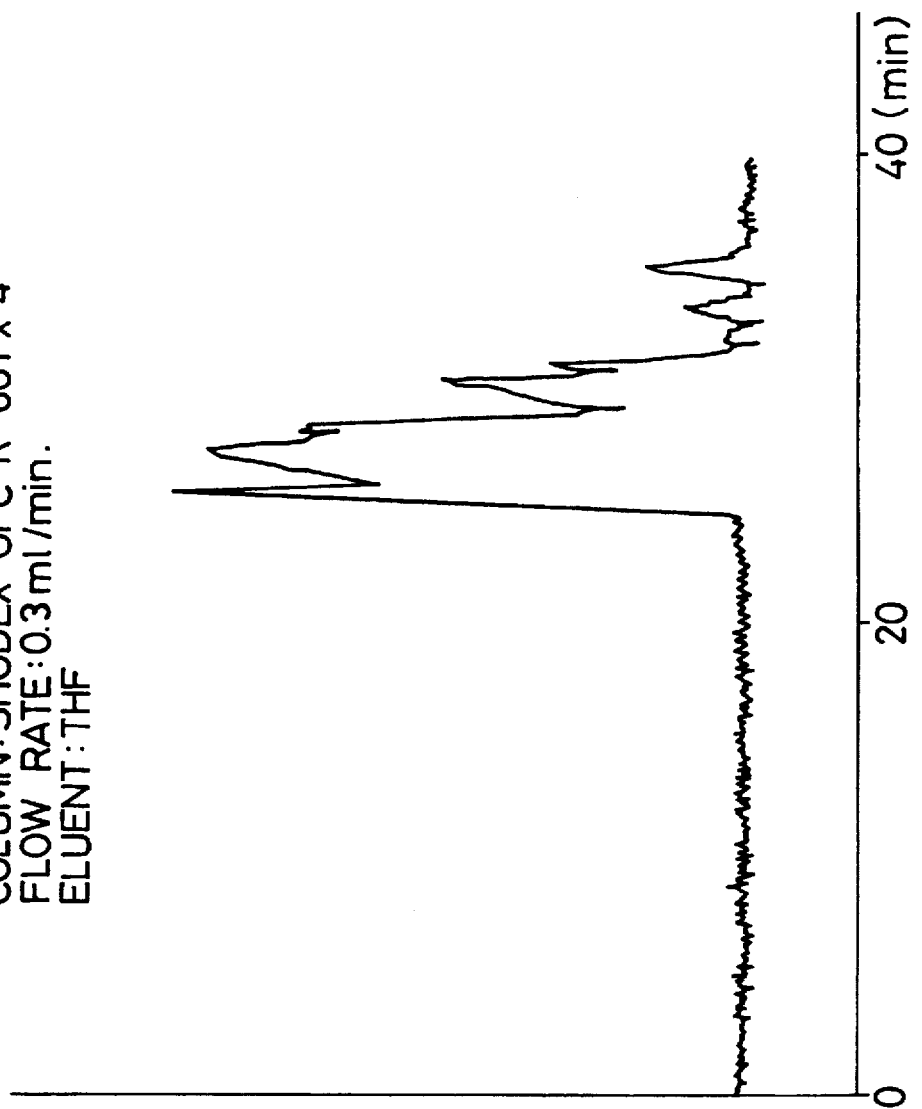
FIG. 6 diagrammatically illustrates the results of a GPC analysis of the resin obtained in Synthesis Example 3.

The resin had a number-average molecular weight of 870 and a carboxylic acid equivalent of 307 g/eq. DTA analysis data and GPC analysis data of the resin are shown in FIGS. 5 and 6, respectively.

SYNTHESIS EXAMPLE 4

Figure 7:
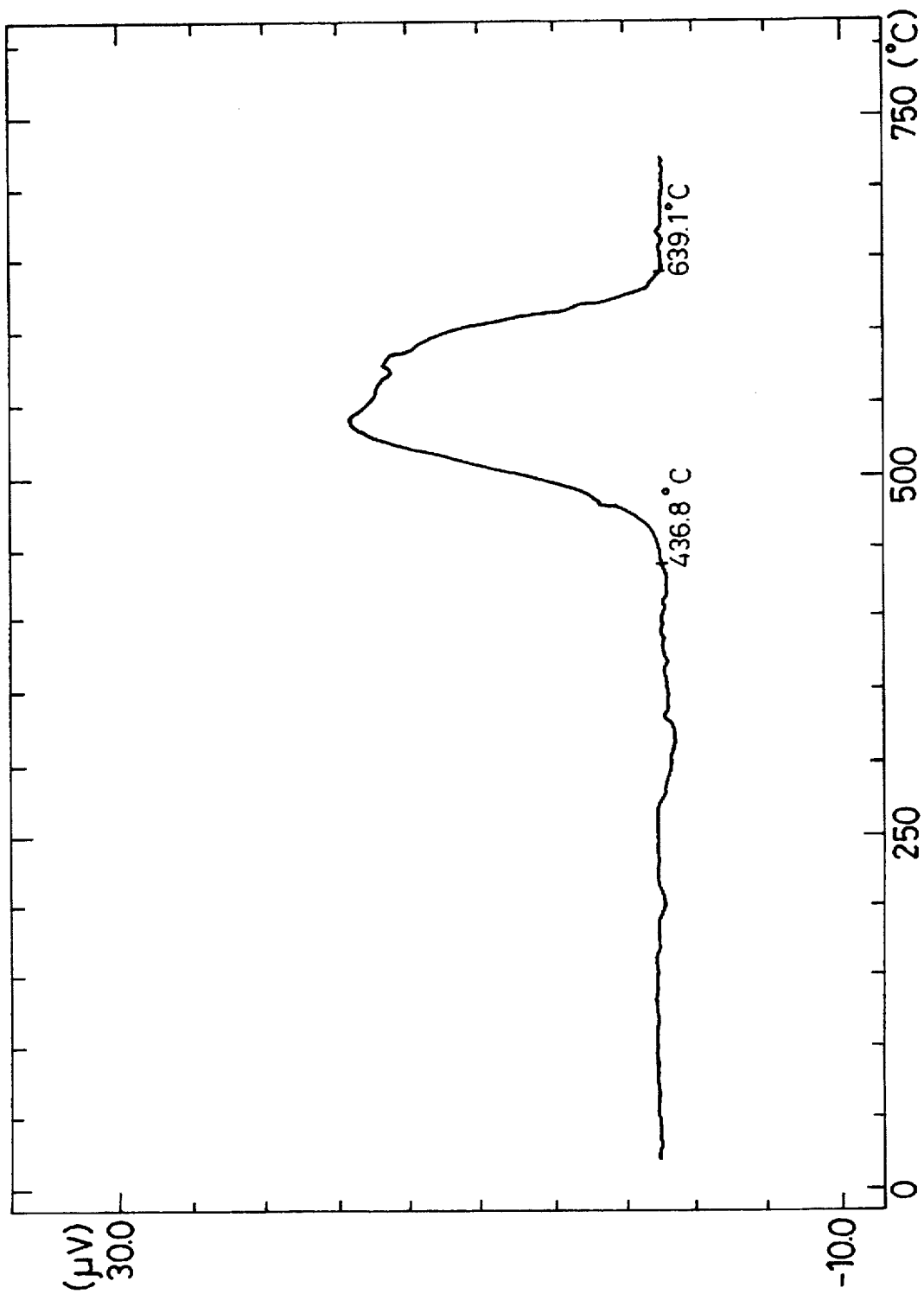
FIG. 7 diagrammatically shows the results of a DTA analysis of the resin obtained in Synthesis Example 4.
Figure 8:
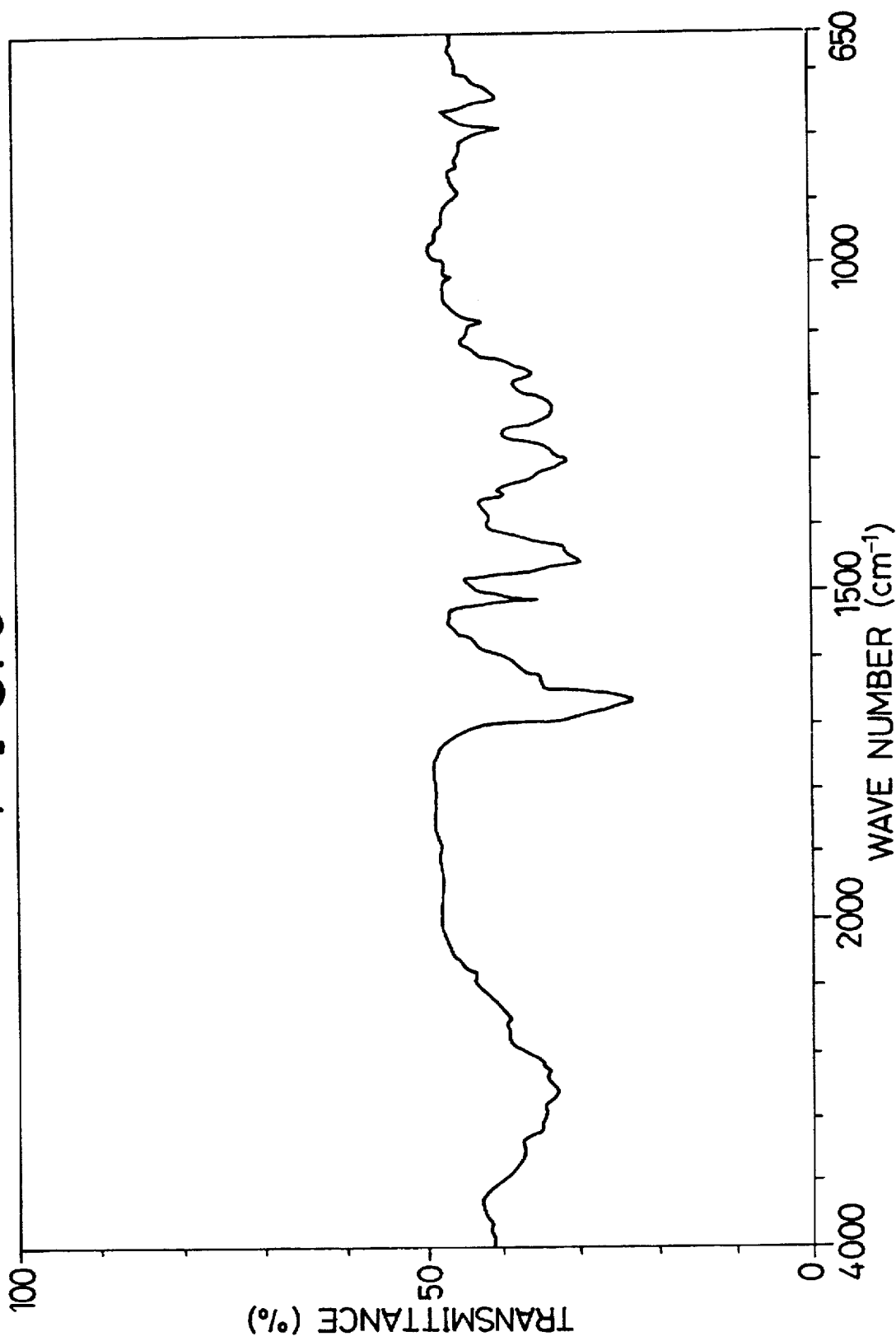
FIG. 8 diagrammatically illustrates the results of an IR analysis of the resin obtained in Synthesis Example 4.

In a reactor equipped with a thermometer and a stirrer, 133 parts (0.74 mol) of 2-hydroxy-3-naphthoic acid, 49 parts (0.355 mol) of salicylic acid, 200 parts of sulfolane and as a catalyst, 0.06 part of trifluoromethanesulfonic acid were charged. To the resulting mixture, 58.9 parts (0.355 mole) of α,α'-dimethoxy-p-xylene were added dropwise at 140°–150° C. over 5 hours, followed by further reaction at 150° C. for 2 hours. The reaction mixture was poured into 1,000 parts of water. The solid so precipitated was collected by filtration and then dried. The resulting solid was charged into 1,500 parts of toluene. After heating and stirring, thermal filtration was repeated three times to remove unreacted raw materials, whereby 148 parts of a hydroxynaphthoic acid co-condensation resin were obtained in a purified form. The resin had a number-average molecular weight of 678 and a carboxylic acid equivalent of 231 g/eq. DTA analysis data and IR measurement results (according to the KBr tablet method) of the resin are shown in FIG. 7 and FIG. 8, respectively.

SYNTHESIS EXAMPLE 5

In a reactor equipped with a thermometer and a stirrer, 913 parts of methyl salicylate were charged, followed by heating to 100°–110° C. At the same temperature, 525 parts of α,α'-dichloro-p-xylene were charged in portions over 5 hours. The resulting mixture was subjected to aging at 150° C. for 2 hours. The pressure of the reactor was reduced to 10 mmHg by a pump and unreacted methyl salicylate was separated for reuse at 150°–180° C. After allowed to cool down to 100° C., 350 ml of toluene were added to the residue, whereby a toluene solution of a salicylic acid ester resin was obtained. In a reactor equipped with a thermometer and a stirrer, 160 parts of caustic soda and 907 parts of water were charged, followed by the dropwise addition of the above-obtained toluene solution at 85°–90° C. over 4 hours. The temperature was raised to 100° C. so that the toluene was distilled off. After removal of insoluble matter, the residue was neutralized with 2,250 parts of an 8% aqueous solution of hydrochloric acid. The solid so precipitated was collected by filtration, washed with water and dried, whereby a salicylic acid resin was obtained in a yield of 705 parts. In a reactor equipped with a thermometer and a stirrer, 100 parts of the salicylic acid resin obtained above [composition (area %) according to a GPC analysis: 51.1% l=0, 22.3% l=1, 20.3% l=2, 4.3% l≧3, 1.0% others; number-average molecular weight: 543], 33.5 parts of benzyl chloride, 400 parts of 1,1,2-trichloroethane and 0.4 part of zinc chloride were charged, followed by reaction at 110° C. for 3 hours. After completion of the reaction, 1,000 parts of water were added and the 1,1,2-trichloroethane was azeotropically distilled off. The solid so precipitated was collected by filtration and dried, whereby 121 parts of an aralkylated salicylic acid resin were obtained. The resin was found to have a number-average molecular weight of 641 and a carboxylic acid equivalent of 251 g/eq.

SYNTHESIS EXAMPLE 6

In a reactor equipped with a thermometer and a stirrer, charged were 200 parts of 2-hydroxy-3-naphthoic acid and 200 parts of o-dichlorobenzene, followed by the addition of 62.1 parts of α,α'-dichloro-p-xylene in portions at 140°–150° C. over 5 hours. The reaction was allowed to proceed further at 150° C. for 2 hours. From the reaction mixture, the o-dichloro-benzene was distilled off by steam distillation. The solid so precipitated was collected by filtration and dried. To the resulting solid, 1 l of methyl isobutyl ketone and 2 l of water were added, followed by the adjustment of pH to 5.9 with an aqueous solution of potassium bicarbonate so that the unreacted 2-hydroxy-3-naphthoic acid was separated out in the water layer. These procedures were repeated three times in total. The organic layer was then washed with 2 l of a 1% aqueous solution of hydrochloric acid, followed by washing with water. The organic solvent was distilled off under reduced pressure, whereby 142 parts of a purified resin were obtained. According to a GPC analysis, the resin was found to have the following composition (area %): 53.0% l=0, 31.0% l=1, 12.1% l≧2 and 1.8% others and also have a carboxylic acid equivalent of 243 g/eq and a number-average molecular weight of 685.

SYNTHESIS EXAMPLE 7

In a reactor equipped with a thermometer and a stirrer, 100 parts of the hydroxynaphthoic acid obtained in Synthesis Example 6, 0.2 part of zinc chloride and 300 parts of sulfolane were charged. The resulting mixture was heated to 100° C., followed by the dropwise addition of 20.4 parts of benzyl chloride at the same temperature over 1 hour. The resulting mixture was stirred under heat at 120° C. for 5 hours, at 130° C. for 2 hours and then at 140° C. for 3 hours. After allowed to cool down, the reaction mixture was poured into 1,500 parts of water. The solid so precipitated was collected by decantation. The resulting solid was added to 1,500 parts of water to form a sludge, followed by removal of the remaining sulfolane. The resulting solid was collected by filtration, washed with water and then dried, whereby 112 parts of an aralkylated hydroxynaphthoic acid resin were obtained. The resin was found to have a number-average molecular weight of 851 and a carboxylic acid equivalent of 291 g/eq.

SYNTHESIS EXAMPLE 8

In a reactor equipped with a thermometer and a stirrer, charged were 133 parts (0.74 mol) of 2-hydroxy-3-naphthoic acid, 49 parts (0.355 mol) of salicylic acid, 200 parts of sulfolane and as a catalyst, 0.1 part of trifluoromethanesulfonic acid. To the resulting mixture, 70.7 parts (0.426 mol) of α,α'-dimethoxy-m-xylene were added dropwise at 140°–150° C. over 5 hours, followed by further reaction at 150° C. for 2 hours. The reaction mixture was poured into 1,000 parts of water. The solid so precipitated was collected by filtration and dried. Methyl isobutyl ketone (1.5 l) and 3 l of water were added to the solid, followed by the adjustment of pH to 5.8 with an aqueous solution of potassium hydrogencarbonate so that the unreacted raw materials were separated out in the water layer. These procedures were repeated three times in total. The organic layer was then washed with 2 l of a 1% aqueous solution of hydrochloric acid and then with water. The organic solvent was distilled off under reduced pressure, whereby 138 parts of a purified resin were obtained. The resin was found to have a number-average molecular weight of 685 and a carboxylic acid equivalent of 239 g/eq.

SYNTHESIS EXAMPLE 9

In a reactor equipped with a thermometer and a stirrer, charged were 50 parts of the hydroxynaphthoic acid obtained in Synthesis Example 2, 22 parts of potassium carbonate and 200 parts of tetrahydrofuran, followed by heating to 70° C. At the same temperature, 20 parts of methyl iodide were added dropwise over 2 hours, followed by stirring under heat for 5 hours. After completion of the reaction, the reaction mixture was poured into 1,000 parts of water. The solid so precipitated was collected by filtration, washed with water and then dried. The resin so obtained was found to have a carboxylic acid equivalent of 265 g/eq.

SYNTHESIS EXAMPLE 10

In an autoclave, charged were 53.0 parts of m-cresol, 25.4 parts of 2,3-xylenol, 51.1 parts of a 37% aqueous solution of formaldehyde, 4.41 parts of oxalic acid dihydrate, 58.5 parts of water and 272 parts of dioxane, followed by stirring under heat at 130° C. for 8 hours. After completion of the reaction, the reaction mixture was cooled down to room temperature and then concentrated in an evaporator, whereby a novolak resin (molecular weight: 8,200) was obtained. This resin will hereinafter be designated as "Novolak Resin (NA)".

SYNTHESIS EXAMPLE 11

In an autoclave, charged were 108.1 parts of m-cresol, 61.1 parts of 2,3-xylenol, 20.5 parts of 3,4-xylenol, 100 parts of a 37% aqueous solution of formaldehyde, 110 parts of water, 700 parts of dioxane and 8.8 parts of oxalic acid dihydrate, followed by stirring under heat at 130° C. for 7 hours. The reaction mixture was then processed as in Synthesis Example 9, whereby a novolak resin (molecular weight: 8,700) was obtained. This resin will hereinafter be designated as "Novolak Resin (NB)".

SYNTHESIS EXAMPLE 12

In a flask equipped with a stirrer, a cooling tube and a thermometer, charged were 64.1 parts of m-cresol, 9.0 parts of 2,3-xylenol, 9.0 parts of 3,4-xylenol, 50.2 parts of a 40% solution of formaldehyde in butanol and 0.5 part of oxalic acid dihydrate, followed by stirring under heat at 100° C. for 2 hours. The volatile matters were thereafter removed at 180° C. and 30–50 mmHg. The residue was cooled down to room temperature, whereby a novolak resin (molecular weight: 9,200) was obtained. This resin will hereinafter be designated as "Novolak Resin (NC)".

SYNTHESIS EXAMPLE 13

In a glass-made reactor equipped with a stirrer, a thermometer and a reflux condenser, 118.1 parts (0.44 mol) of 1,2-diazidonaphthoquinone-4-sulfonic acid chloride and 20.2 parts (0.1 mol) of 4,4'-dihydroxybenzophenone were dissolved in 300 parts of dimethylacetoamide, followed by the dropwise addition of 21.2 parts of triethylamine over 30 minutes under stirring. Stirring was continued for further 2 hours. After the resulting precipitate was filtered off, 250 parts of a 1% aqueous solution of hydrochloric acid were added dropwise to the thus-obtained filtrate so that a reaction product was caused to precipitate. The precipitate was collected by filtration, washed with water and then dried. According to a GPC analysis, the resulting product, that is, a photosensitizer, was found to have a purity of 99.5%. This photosensitizer will hereinafter be designated as "Photosensitizer (A)".

SYNTHESIS EXAMPLE 14

In a similar manner as Synthesis Example 13, a photosensitizer was synthesized using 1 mole of 1,3,3-tris(4-hydroxyphenyl)butane and 2.5 moles of 1,2-diazidonaphthoquinone-5-sulfonic acid chloride. According to a GPC analysis, the photosensitizer was found to have a purity of 99.8%. This photosensitizer will hereinafter be designated as "Photosensitizer (B)".

SYNTHESIS EXAMPLE 15

In a similar manner as Synthesis Example 13, a photosensitizer was synthesized using 1 mole of 1,1,3-tris(2,5-dimethyl-4-hydroxyphenyl)butane and 2.5 moles of 1,2-diazidonaphthoquinone-4-sulfonic acid chloride. According to GPC, the photosensitizer was found to have a purity of 99.3%. This photosensitizer will hereinafter be designated as "Photosensitizer (C)".

EXAMPLE 1

In 48 parts of Ethyl Cellosolve acetate, 17 parts of the resin obtained in Synthesis Example 1 and 5 parts of Photosensitizer (A) were dissolved. The resulting solution was filtered through a 0.2 μm Teflon filter to formulate a resist composition. The resist composition was coated on a silicon wafer, which had been washed in a manner known per se in the art, by a spin coater to give a film thickness of 1.2 μm. The silicon wafer so coated was baked on a hot plate of 100° C. for 60 seconds.

Using a reduction projection aligner ("DSW4800", trade name; manufactured by GCA, NA=0.28) having an exposure wavelength of 436 nm (g-rays), the wafer was then exposed while varying the exposure stepwise. The wafer was developed for one minute in a 2% choline solution, whereby a positive pattern was obtained. The standardized film thickness (=remaining film thickness/initial film thickness) was plotted versus the logarithm of exposure to determine the gradient 0, whereby tan θ was recorded as a "γ value". The "γ value" was found to be 4.3.

EXAMPLE 2

In a similar manner as Example 1 except that 17 parts of the resin obtained in Synthesis Example 2 and 5 parts of Photosensitizer (A) were employed, a resist pattern was formed. The resist pattern so formed was found to have a a value of 4.1.

EXAMPLE 3

In a similar manner as Example 1 except that 17 parts of the resin obtained in Synthesis Example 3 and 5 parts of Photosensitizer (A) were employed, a resist pattern was formed. The resist pattern so formed was found to have a γ value of 4.2.

EXAMPLE 4

In a similar manner as Example 1 except that 17 parts of the resin obtained in Synthesis Example 4 and 5 parts of Photosensitizer (A) were employed, a resist pattern was formed. The resist pattern so formed was found to have a γ value of 4.2.

Comparative Example 1

In a similar manner as Example 1 except that 17 parts of Novolak Resin (NA) and 5 parts of Photosensitizer (A) were employed, a resist pattern was formed. The resist pattern so formed was found to have a γ value of 2.0.

EXAMPLES 5–26

In each Example, an alkaline-soluble resin and a photosensitizer shown in Table 1 were dissolved in 48 parts of ethyl cellosolve acetate. The resulting solution was filtered through a 0.2 μm Teflon filter to formulate a resist composition. The resist composition was coated on a silicon wafer, which had been washed in a manner known per se in the art, by a spin coater to give a film thickness of 1.2 μm. The silicon wafer so coated was then baked on a hot plate of 100° C. for 60 seconds.

The wafer was then exposed using a reduction projection aligner ("NSR-1755li7A", trade name; manufactured by NIKON CORP, NA=0.50) having an exposure wavelength of 365 nm (i-rays). The wafer was then baked for one minute on a hot plate controlled at 110° C. The resulting wafer was developed for one minute in a 2.4 wt. % aqueous solution of tetramethylammoniumhydroxide, whereby a positive pattern was obtained. The resist pattern so obtained was evaluated. The results are shown in Table 1. As shown in Table-1, the resist pattern had good focus latitude, sensitivity, definition, developability, pattern shape and heat resistance.

Comparative Example 2

In a similar manner as Example 5 except that 17 parts of Novolak Resin (NB) and 5 parts of Photosensitizer (A) were employed, a resist pattern was formed. The evaluation results of the resist pattern so obtained are shown in Table 1.

TABLE 1

(1-1)

alkaline-solution-soluble components

| Ex. | A | Xylylene group | Average l | n | m | Parts by weight Formula (1) | Another resin | Photo-sensitive component |
|---|---|---|---|---|---|---|---|---|
| 5 | HOOC—[phenyl with OH and CH₃]— | p-xylylene group | 2 | 0 | 0 | 2 | NA 10 | A |
| 6 | " | m-xylylene group | 2 | 0 | 0 | 2 | NB 10 | A |
| 7 | HOOC—[phenyl with OH]— | p-xylylene group | 1 | 1 | 5 | 1 | NC 11 | B |
| 8 | 41 | m-xylylene group | 1 | 0 | 0 | 3 | NA 9 | B |

(1-2)

Evaluation results

| Ex. | Sensitivity (msec) | Resolution | Focus latitude | Developability | Pattern | Heat resistance |
|---|---|---|---|---|---|---|
| 5 | 410 | A | A | A | A | A |
| 6 | 405 | A | A | A | A | A |
| 7 | 420 | A | A | A | A | A |
| 8 | 415 | A | A | A | A | A |

TABLE 1-continued

(2-1)

alkaline-solution-soluble components

| Ex. | A | Xylylene group | Average l | n | m | Parts by weight Formula (1) | Another resin | Photo-sensitive component |
|---|---|---|---|---|---|---|---|---|
| 9 | HOOC—⌬(OH)—C₂H₅ | p-xylylene group | 1.5 | 2 | 10 | 4 | NC 8 | C |
| 10 | " | m-xylylene group | 2 | 0 | 0 | 1 | NA 11 | A |
| 11 | HO—⌬⌬—COOH (naphthalene) | p-xylylene group | 2.5 | 0 | 0 | 1 | NC 11 | B |
| 12 | " | o-xylylene group | 1 | 1 | 6 | 0.5 | NA 11.5 | A |

(2-2)

Evaluation results

| Ex. | Sensitivity (msec) | Resolution | Focus latitude | Developability | Pattern | Heat resistance |
|---|---|---|---|---|---|---|
| 9 | 410 | A | A | A | A | A |
| 10 | 405 | A | A | A | A | A |
| 11 | 405 | A | A | A | A | A |
| 12 | 420 | A | A | A | A | A |

(3-1)

alkaline-solution-soluble components

| Ex. | A | Xylylene group | Average l | n | m | Parts by weight Formula (1) | Another resin | Photo-sensitive component |
|---|---|---|---|---|---|---|---|---|
| 13 | HO—⌬⌬—COOH / HO—⌬—COOH = 1/1 | p-xylylene group | 0 | 0 | 0 | 1 | NB 11 | C |
| 14 | " | m-xylylene group | 1 | 2 | 10 | 2 | NB 10 | C |

TABLE 1-continued

| 15 |  HOOC—OH | p-xylyle-ne group | 10 | 0 | 0 | 12 | — | B |
| 16 |  HO—COOH | p-xylyle-ne group | 10 | 0 | 4 | 12 | — | C |

(3-2)

| | Evaluation results | | | | | |
|---|---|---|---|---|---|---|
| Ex. | Sensitivity (msec) | Resolution | Focus latitude | Developa- bility | Pattern | Heat resistance |
| 13 | 425 | A | A | A | A | A |
| 14 | 415 | A | A | A | A | A |
| 15 | 420 | A | A | A | A | A |
| 16 | 405 | A | A | A | A | A |

(4-1)

| | alkaline-solution-soluble components | | | | | Parts by weight | | Photo- |
|---|---|---|---|---|---|---|---|---|
| Ex. | A | Xylylene group | l | n | m | Average Formula (1) | Another resin | sensitive component |
| 17 |  HO—COOH(orCH₃)  Esterification degree = 10% | p-xylyle-ne group | 0 | 0 | 0 | 2 | NA 10 | B |
| 18 | " | m-xylyle-ne group | 0 | 0 | 3 | 1 | NB 11 | B |
| 19 |  HO—COOH(orCH₃) / 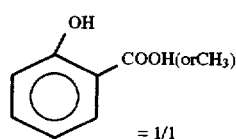 OH—COOH(orCH₃) = 1/1  Esterification degree = 15% | p-xylyle-ne group | 1.5 | 0 | 0 | 2 | NC 10 | C |

TABLE 1-continued

| | | | | | | | | |
|---|---|---|---|---|---|---|---|---|
| 20 | " | m-xylylene group | | 2 | 1 | 5 | 3 | NC 9 | C |

(4-2)

| | Evaluation results | | | | | |
|---|---|---|---|---|---|---|
| Ex. | Sensitivity (msec) | Resolution | Focus latitude | Developability | Pattern | Heat resistance |
| 17 | 405 | A | A | A | A | A |
| 18 | 410 | A | A | A | A | A |
| 19 | 410 | A | A | A | A | A |
| 20 | 415 | A | A | A | A | A |

(5-1)

| | alkaline-solution-soluble components | | | | | | Photo- |
|---|---|---|---|---|---|---|---|
| | | | Average | | | Parts by weight | sensitive |
| Ex. | A | Xylylene group | l | n | m | Formula (1) | Another resin | component |
| 21 | 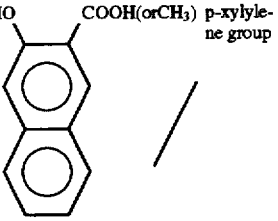 HO COOH(orCH$_3$) / OH COOH = 3/1 | p-xylylene group | 1 | 1 | 6 | 4 | NA 8 | A |
| 22 | " | m-xylylene group | 2 | 0 | 0 | 4 | NA 8 | A |
| 23 | 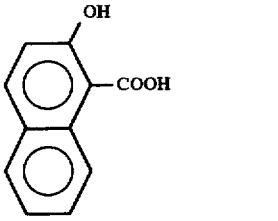 HO COOH (orC$_2$H$_5$) Esterification degree = 20% | p-xylylene group | 0 | 0 | 0 | 2 | NC 10 | C |
| 24 | " Esterification degree = 30% | p-xylylene group | 1.5 | 0 | 0 | 3 | NB 9 | C |

(5-2)

| | Evaluation results | | | | | |
|---|---|---|---|---|---|---|
| Ex. | Sensitivity (msec) | Resolution | Focus latitude | Developability | Pattern | Heat resistance |
| 21 | 420 | A | A | A | A | A |
| 22 | 410 | A | A | A | A | A |
| 23 | 420 | A | A | A | A | A |
| 24 | 430 | A | A | A | A | A |

TABLE 1-continued (6-1)
alkaline-solution-soluble components

| Ex. | A | Xylylene group | Average 1 | n | m | Parts by weight Formula (1) | Another resin | Photo-sensitive component |
|---|---|---|---|---|---|---|---|---|
| 25 | HO—[naphthalene]—COOH, OH | p-xylylene group | 2 | 1 | 5 | 3 | NA 9 | A |
| 26 | " | m-xylylene group | 10 | 0 | 0 | 12 | — | A |
| Comp. Ex. 2 | — | — | — | — | — | — | NB 12 | A |

(6-2)
Evaluation results

| Ex. | Sensitivity (msec) | Resolution | Focus latitude | Developability | Pattern | Heat resistance |
|---|---|---|---|---|---|---|
| 25 | 420 | A | A | A | A | A |
| 26 | 405 | A | A | A | A | A |
| Comp. Ex. 2 | 505 | B | B | B | B | B |

Evaluation of Resist

Sensitivity

Using a reduction projection aligner ("NSR-1755li7A", trade name; manufactured by NIKON CORP; NA=0.50), each resist-coated wafer was exposed to i-rays of 365 nm wavelength while changing the time of exposure. The wafer was then developed at 25° C. for 60 seconds in a 2.4 wt. % aqueous solution of tetramethylammonium hydroxide to form a positive resist on the wafer. An optimal exposure time [the exposure time which formed a line-and-space (1L1S) pattern of a line width of 0.35 µm at a 1:1 width ratio] was recorded as the sensitivity.

Resolving power

The dimension of a smallest resist pattern successfully resolved when exposed for the optimal exposure time was recorded as the resolving power. Samples having a dimension equivalent to those of the Comparative Examples were rated as "B", while those having a smaller dimension were rated as "A".

Focus latitude

Each 1L1S pattern of a line width of 0.35 µm was observed under a scanning electron microscope. The focus latitude was evaluated from a shift of a focal point where the dimension of the pattern resolved was within±10% of the dimension of mask and the percentage of a film thickness after development of a resist pattern based on a film thickness of the resist pattern before the development (percent film remainder) was 90% or greater. Samples having a focus latitude equivalent to those of the Comparative Examples were rated as "B", while those having a greater focus latitude were rated as "A".

Developability

Developability was evaluated under a scanning electron microscope. Samples having less scum and/or undeveloped portions than the samples of the Comparative Examples were rated as "A", while those similar in this respect to the samples of the Comparative Examples were rated as "B".

Pattern shape

The dimension L1 of a lower side of a square cross-section of each 1L1S pattern of a line width of 0.35 µm and the dimension L2 of its upper side were measured under a scanning electron microscope. Each sample was rated as "A" when the ratio of L2 to L1 fell within a range of from 0.85 to 1, both inclusive, (i.e., $0.85 \leq L2/L1 \leq 1$) and vertical sides are perpendicular to both the lower and upper sides.

Heat resistance

Each wafer with a resist pattern formed thereon was heated at 130° C. for 2 minutes in an oven. When the pattern was not deformed, the corresponding resist sample was rated as "A".

EXAMPLE 27

The resin (10 g) obtained in Synthesis Example 1 was ground and then dispersed in 100 g of a 0.8% aqueous solution of caustic soda. Under stirring, the dispersion was heated to 70° C. to dissolve the resin. While maitaining the resulting solution at 30°–35° C., a solution, which had been obtained in advance by dissolving 2.0 g of anhydrous zinc chloride in 30 ml of water, was added dropwise over 30 minutes under stirring so that a white precipitate appeared.

Stirring was continued at the same temperature for further 2 hours, followed by filtration, washing with water and drying, whereby 9.8 g of white powder were obtained. The white powder so obtained was the zinc salt of the resin. It was found to have a zinc content of 7.0%.

A suspension was formulated by employing as a color-developing agent the above-obtained metal-modified salt of the resin and dispersing the following composition in a sand grinding mill.

|  | Parts by weight |
| --- | --- |
| Color-developing agent | 6 |
| 10% Aq. soln. of polyvinyl alcohol ["Kuraray #117", trade name; product of KURARAY CO., LTD.] | 3 |
| Water | 22.5 |

Using the suspension obtained above, a coating formulation of the following composition was next prepared.

|  | Parts by weight |
| --- | --- |
| Suspension | 10 |
| Light calcium carbonate | 10 |
| Starch | 0.8 |
| Synthetic rubber latex | 0.8 |
| Water | 32.5 |

The coating formulation was coated on a wood free paper web to give a dry coat weight of 5.0–5.5 g/m$^2$, followed by drying to obtain color-developing sheets. The color-developing sheets were evaluated by the method to be described below. The results are shown in Table 2.

TABLE 2

| Example |  |  | Ex. 27 | Comp. Ex. 3 |
| --- | --- | --- | --- | --- |
| Yellowing before test (WB value) |  |  | 84.5 | 84.8 |
| NO$_x$ yellowing of color developing sheet (WB value) |  |  | 81.8 | 80.1 |
| Light yellowing of color developing sheet (WB value) |  |  | 80.5 | 80.6 |
| Production of blue color 20° C./65% RH | Produced color density of color developing sheet (Y) | 30 sec later | 56.1 | 58.0 |
|  |  | 24 hrs later | 50.5 | 55.7 |
|  | Light fastness of produced color image (Y) | 2 hrs later | 63.2 | 62.7 |
|  |  | 4 hrs later | 71.3 | 72.1 |
| Plasticizer resistance of produced color image (Y) |  |  | 50.5 | 59.1 |
| Water proofness of produced color image |  |  | Good | Disappeared |
| Color production at low temperatures 5° C./60% RH | Produced color density of color developing sheet (Y) | 1.5 min later | 59.0 | 70.1 |
|  |  | 24 hrs later | 50.9 | 56.8 |

Evaluation method of properties of color-developing sheets for pressure-sensitive copying papers 1. Color-producing speed and produced color density (conducted in a room air-conditioned at 20° C. and 65% RH)

In the case of blue color production, a commercial blue-color producing CB-sheet ("NW-40T", trade name; product of Jujo Paper Co., Ltd.) containing crystal violet lactone (CVL) as a principal pressure-sensitive dyestuff precursor was used. It was stacked on a sample color-developing sheet (CF-sheet) coated with a water-base coating formulation with their coated sides maintained in a contiguous relation. The thus-stacked pressure-sensitive copying paper was typed by an electric typewriter to produce a color.

The reflectance of the sample color-developing sheet was measured twice, namely, 30 seconds and 24 hours after the typing, by a "Σ-80" color difference meter (manufactured by Tokyo Denshoku Kogyo K. K.). The results were expressed in terms of Y value.

2. Light fastness of produced color marks

Each sample color-developing sheet, which had produced a color in the above-described manner, was exposed for 2 hours (or for 4 hours) to light on a carbon arc fadeometer (manufactured by Suga Testing Machine Co., Ltd.). After the exposure, its density was measured by the "Σ-80" color difference meter. The results were expressed in terms of Y value. The smaller the Y value and the smaller its difference from the Y value before the test, the less the fading by light and the more preferable.

3. Plasticizer resistance

DOP microcapsule coated paper sheets were prepared by forming microcapsules with dioctyl phthalate (DOP) contained as a core substance, equipped with a melamine-formaldehyde resin capsule wall and having an average capsule size of 5.0 µm, adding a small amount of a starch-type binder to the microcapsules, applying the thus-prepared coating formulation onto a wood free paper web by an air-knife coater to give a dry coat weight of 5 g/m$^2$, and then drying the thus-coated paper web. One of the DOP microcapsule coated paper sheets and the color-developing sheet which had been colored by the Testing Method 1 were brought into a contiguous relation with their coated sides facing each other. They were thereafter caused to pass under a linear pressure of 100 kg/cm through a super calender roll, so that DOP was allowed to penetrate uniformly into the colored surface.

One hour after the test, the density of the color-developing sheet was measured by the "Σ-80" color difference meter. The results were expressed in terms of Y value. The smaller the Y value and the smaller its difference from the Y value before the test, the better the plasticizer resistance of the produced color marks.

4. Waterproofness of produced color marks

Each sample color-developing sheet, which had been colored by Testing Method 1, was dipped for 2 hours in water. Density changes of the produced color marks were observed visually.

5. Yellowing tendency of color-developing sheets (5–1) Yellowing by NO$_X$

Following JIS L-0855 (Testing Method for NO$_X$ Gas Fastness of Dyed Materials and Dyes), each sample color-developing sheet was stored for 1 hour in a closed vessel of an atmosphere of NO$_x$ occurred by the reaction of NaNO$_2$ (sodium nitrite) and phosphoric acid. The degree of its yellowing was investigated.

Upon an elapsed time of 1 hour after completion of the test, the density of the color-developing sheet was measured by the "Σ-80" color difference meter. The measurement results were expressed in terms of WB value. The greater the WB value and the smaller its difference from the WB value before the test, the smaller the yellowing tendency in an NO$_X$ atmosphere.

(5–2) Yellowing by exposure to light

Each sample color-developing sheet was exposed for 4 hours to light on the carbon arc fadeometer (manufactured by Suga Testing Machine Co., Ltd.). After the exposure, the density of the sample color-developing sheet was measured by the "Σ-80" color difference meter. The measurement results are expressed in terms of WB value. The greater the WB value and the smaller its difference from the WB value before the test, the smaller the yellowing tendency upon exposure to light.

Comparative Example 3

As in Example 27, color-developing sheets were produced using zinc 3,5-di-tert-butylsalicylate and their evaluation was conducted. Evaluation results are shown in Table 2.

EXAMPLES 28–30

In each Example, a resin metal salt in Table 3 was synthesized and color-developing sheets were fabricated therefrom as in Example 27. The color-developing sheets so obtained were subjected to property evaluation tests as in Example 27. The test results are summarized in Table 3.

TABLE 3 (1)

| Example | Example 28 | Example 29 | Example 30 |
|---|---|---|---|
| Compound | Obtained in Synthesis Example 2 | Obtained in Synthesis Example 3 | Obtained in Synthesis Example 4 |
| Zn content (%) | 7.1 | 7.0 | 7.3 |
| Yellowing before test (WB value) | 85.0 | 84.9 | 85.0 |

TABLE 3 (1)-continued

| Example | | | Example 28 | Example 29 | Example 30 |
|---|---|---|---|---|---|
| $NO_x$ yellowing of color developing sheet (WB value) | | | 82.0 | 81.9 | 82.0 |
| Light yellowing of color developing sheet (WB value) | | | 80.3 | 80.7 | 80.3 |
| Production of blue color 20° C./ 65% RH | Produced color density of color developing sheet (Y) | 30 sec later | 56.0 | 56.5 | 56.3 |
| | | 24 hrs later | 50.0 | 50.5 | 50.3 |
| | Light fastness of produced color image (Y) | 2 hrs later | 63.5 | 63.2 | 63.1 |
| | | 4 hrs later | 72.1 | 71.3 | 72.1 |
| Plasticizer resistance of produced color image (Y) | | | 50.8 | 50.0 | 50.7 |
| Water proofness of produced color image | | | Good | Good | Good |
| Color production at low temperatures 5° C./ 60% RH | Produced color density of color developing sheet (Y) | 1.5 min later | 58.3 | 59.3 | 59.2 |
| | | 24 hrs later | 50.1 | 50.7 | 50.8 |

EXAMPLES 31–40

In each example, a resin metal salt shown in Table 4 was synthesized and color developing sheets were produced therefrom as in Example 27. The color-developing sheets so obtained were subjected to property evaluation tests as in Example 27. The test results are shown in Table 5.

TABLE 4

| Comp'd A | | Xylylene group | Average | | | Metal | Metal content (%) |
|---|---|---|---|---|---|---|---|
| | | | l | n | m | Metal | (%) |
| a | 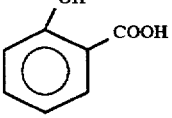 | m-xylylene group | 0 | 0 | 3 | Zn | 7.3 |
| b | 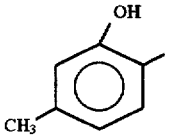 | p-xylylene group | 1 | 1 | 10 | Zn | 7.0 |
| c | 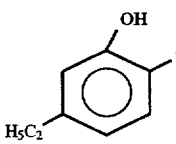 | p-xylylene group | 0 | 2 | 15 | Zn | 6.5 |
| d | 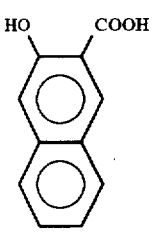 | p-xylylene group | 0 | 1 | 10 | Zn | 7.3 |

TABLE 4-continued
| Comp'd A | | Xylylene group | Average l | n | m | Metal | Metal content (%) |
|---|---|---|---|---|---|---|---|
| e | 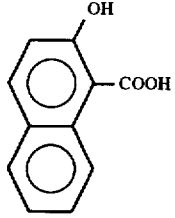 | p-xylylene group | 0 | 0 | 3 | Zn | 6.8 |
| f | 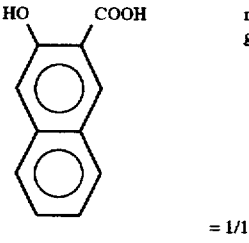 = 1/1 | m-xylylene group | 1 | 0 | 3 | Zn | 6.5 |
| g | 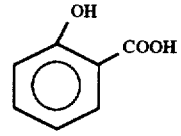 | m-xylylene group | 1 | 1 | 10 | Zn | 7.5 |
| h | 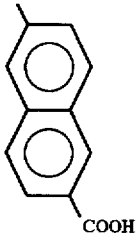 | m-xylylene group | 0 | 1 | 5 | Zn | 7.2 |
| i |  | m-xylylene group | 0 | 0 | 3 | Zn | 7.1 |
| j | " | p-xylylene group | 0 | 1 | 10 | Zn | 8.0 |

TABLE 5

|  |  |  | Example | | | | |
|---|---|---|---|---|---|---|---|
|  |  |  | 31 | 32 | 33 | 34 | 35 |
| Compound |  |  | a | b | c | d | e |
| Yellowing before test (WB value) |  |  | 85.0 | 85.1 | 85.0 | 85.2 | 85.0 |
| $NO_x$ yellowing of color developing sheet (WB value) |  |  | 82.1 | 82.0 | 82.1 | 82.3 | 82.0 |
| Light yellowing of color developing sheet (WB value) |  |  | 80.5 | 80.4 | 80.2 | 80.3 | 80.5 |
| Production of blue color 20° C./65% RH | Produced color density of color developing sheet (Y) | 30 sec later | 56.5 | 56.4 | 56.3 | 56.2 | 56.5 |
|  |  | 24 hrs later | 51.1 | 50.8 | 50.7 | 50.1 | 50.8 |
|  | Light fastness of produced color image (Y) | 2 hrs later | 63.2 | 63.3 | 63.5 | 63.5 | 63.1 |
|  |  | 4 hrs later | 71.8 | 71.5 | 71.8 | 72.0 | 71.9 |
| Plasticizer resistance of produced color image (Y) |  |  | 50.7 | 50.8 | 50.1 | 50.6 | 50.8 |
| Water proofness of produced color image |  |  | Good | Good | Good | Good | Good |
| Color production at low temperatures 5° C./60% RH | Produced color density of color developing sheet (Y) | 1.5 min later | 58.2 | 58.1 | 58.3 | 58.4 | 58.1 |
|  |  | 24 hrs later | 50.5 | 50.4 | 50.3 | 50.1 | 50.1 |

|  |  |  | Example | | | | |
|---|---|---|---|---|---|---|---|
|  |  |  | 36 | 37 | 38 | 39 | 40 |
| Compound |  |  | f | g | h | i | j |
| Yellowing before test (WB value) |  |  | 85.1 | 85.1 | 85.0 | 85.1 | 85.2 |
| $NO_x$ yellowing of color developing sheet (WB value) |  |  | 82.2 | 82.0 | 82.5 | 82.3 | 82.1 |
| Light yellowing of color developing sheet (WB value) |  |  | 80.4 | 80.3 | 80.4 | 80.5 | 80.6 |
| Production of blue color 20° C./65% RH | Produced color density of color developing sheet (Y) | 30 sec later | 56.4 | 56.3 | 56.2 | 56.3 | 56.1 |
|  |  | 24 hrs later | 50.5 | 50.8 | 50.2 | 50.1 | 51.3 |
|  | Light fastness of produced color image (Y) | 2 hrs later | 63.2 | 63.3 | 63.4 | 63.5 | 63.0 |
|  |  | 4 hrs later | 72.1 | 72.3 | 71.8 | 71.6 | 72.1 |
| Plasticizer resistance of produced color image (Y) |  |  | 50.9 | 50.1 | 50.0 | 50.7 | 51.0 |
| Water proofness of produced color image |  |  | Good | Good | Good | Good | Good |
| Color production at low temperatures 5° C./60% RH | Produced color density of color developing sheet (Y) | 1.5 min later | 58.2 | 58.3 | 58.5 | 58.6 | 58.1 |
|  |  | 24 hrs later | 50.9 | 50.9 | 50.3 | 50.5 | 50.3 |

As is apparent from the results shown in Table 1, a photopolymer composition comprising the hydroxycarboxylic acid resin according to the present invention is suited for the formation of high-resolution positive patterns. Compared with compositions containing conventional novolak resins as alkaline-solution-soluble resins, it can provide minute patterns excellent in processing accuracy. The composition can therefore meet the demand from the industrial field of semi-conductor devices for the fabrication of semi-conductor devices of higher integration Further, as is evident from Tables 3–5, each metal-modified hydroxycarboxylic acid resin according to the present invention is useful as a color-developing agent and can provide color-developing sheets excellent in $NO_X$ yellowing resistance, light yellowing resistance, plasticizer resistance and water proofness.

What is claimed is:

1. An aromatic hydroxycarboxylic acid resin having a number-average molecular weight of 370–50.000 and being represented by the following formula (1):

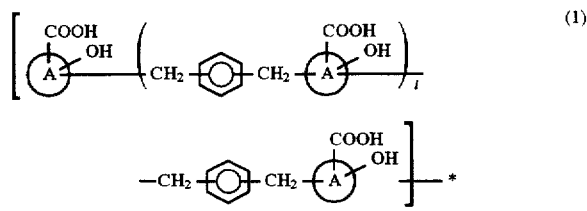

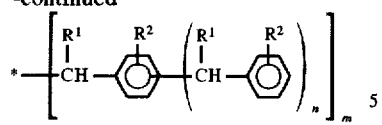

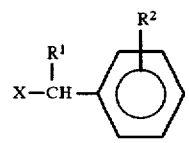

wherein each A group is the same or different and individually represents a substituted or unsubstituted phenylene or naphthylene group. $R^1$ represents a hydrogen atom or a $C_{1-4}$ alkyl Group. $R^2$ represents a hydrogen atom. l stands for an integer of 0–100, m stands for an integer of 0–20 and n stands for an integer of 0–3 with the proviso that m stands for an integer other than 0 when all of the A groups represent a substituted or unsubstituted phenylene group.

2. A resin according to claim 1, which is an aralkylated salicylic acid resin represented by the following formula (2):

wherein $R^1$ represents a hydrogen atom or a $C_{1-4}$ alkyl group. $R^2$ represents a hydrogen atom and X represents a halogen atom, at an aralkyl compound/salicylic acid resin weight ratio of from 0.01 to 10.

4. A resin according to claim 1, which is an aralkylated hydroxynaphthoic acid resin represented by the following formula (3):

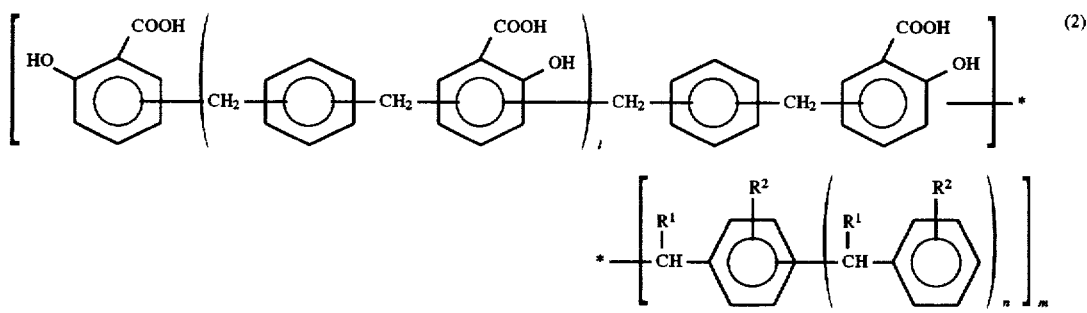

wherein $R^1$ represents a hydrogen atom or a $C_{1-4}$ alkyl group. $R^2$ represents a hydrogen atom, l stands for an integer of 0–100, m stands for an integer of 1–20 and n stands for an integer of 0–3, and having a number-average molecular weight of 450–20,000 and a carboxylic acid equivalent of 245–440 g/eq.

3. A process for the production of a resin of claim 2, which comprises reacting a salicylic acid resin represented by the following formula (8):

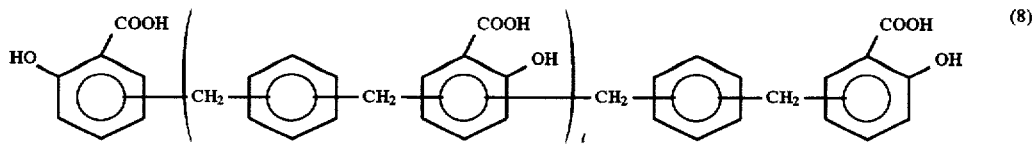

wherein l stands for an integer of 0–100 with an aralkyl compound represented by the following formula (9):

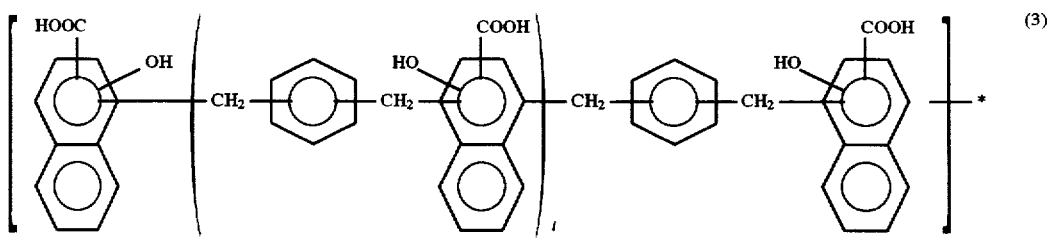

-continued

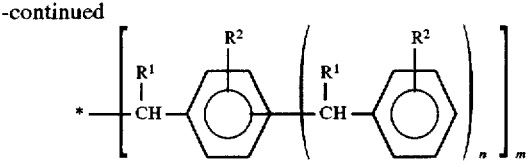

wherein $R^1$ represents a hydrogen atom or a $C_{1-4}$ alkyl group, $R^2$ represents a hydrogen atom, l stands for an integer of 0–100, m stands for an integer of 1–20 and n stands for an integer of 0–3, and having a number-average molecular weight of 510–20,000 and a carboxylic acid equivalent of 232–400 g/eq.

5. A process for the preparation of a resin of claim 4, which comprises reacting a hydroxynaphthoic acid resin represented by the following formula (10):

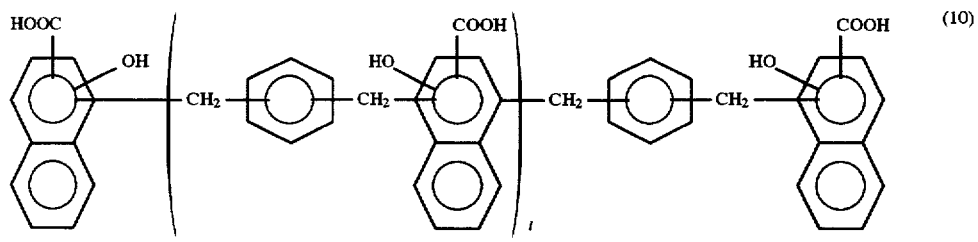

wherein l stands for an integer of 0–100 with an aralkyl compound represented by the following formula (9):

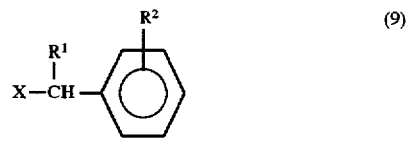

wherein $R^1$ represents a hydrogen atom or a $C_{1-4}$ alkyl group, $R^2$ represents a hydrogen atom and X represents a halogen atom, at an aralkyl compound/hydroxynaphthoic acid resin weight ratio of from 0.01 to 10.

6. A resin according to claim 1, which is a hydroxynaphthoic acid resin represented by the following formula (4):

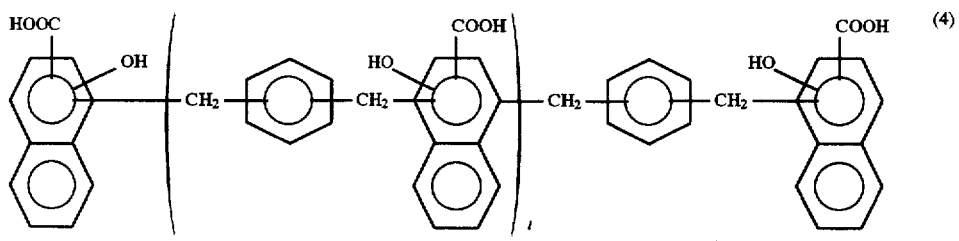

wherein l stands for an integer of 0–100, and having a number-average molecular weight of 500–50,000 and a carboxylic acid equivalent of 240–288 g/eq.

7. A process for the preparation of a resin of claim 6, which comprises reacting hydroxynaphthoic acid represented by the following formula (5):

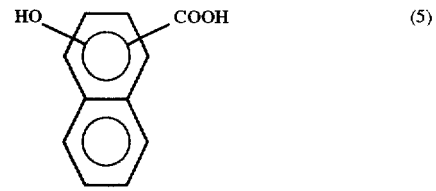

with a xylylene compound represented by the following formula (7):

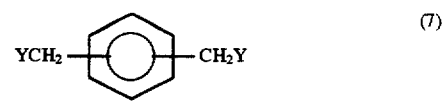

wherein Y represents a halogen atom or a hydroxyl or $C_{1-4}$ alkoxyl group, at a xylylene compound/hydroxynaphthoic acid mole ratio of from 0.1 to 1.0.

8. A resin according to claim 1, which is a hydroxynaphthoic acid co-condensation resin obtained by reacting hydroxynaphthoic acid represented by the following formula (5):

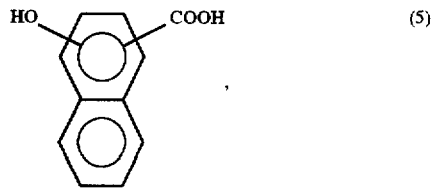

a hydroxybenzoic acid represented by the following formula (6):

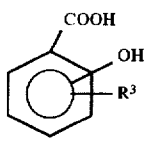

wherein $R^3$ represents a hydrogen atom or a $C_{1-10}$ alkyl group, and a xylylene compound represented by the following formula (7):

wherein Y represents a halogen atom, a hydroxyl group or a $C_{1-4}$ alkoxy group, the molar ratio of the xylylene compound to the sum of the hydroxynaphthoic acid and the hydroxybenzoic acid falling within a range of 0.1 to 1.0 and the molar ratio of the hydroxynaphthoic acid to the hydroxybenzoic acid falling within a range of from 0.01 to 100; and having a number-average molecular weight of 370–50,000.

9. A partial esterification product obtained by partially esterifying carboxyl groups in a hydroxycarboxylic acid resin having a number-average molecular weight in the range of 370–50,000 and being represented by the following formula (11):

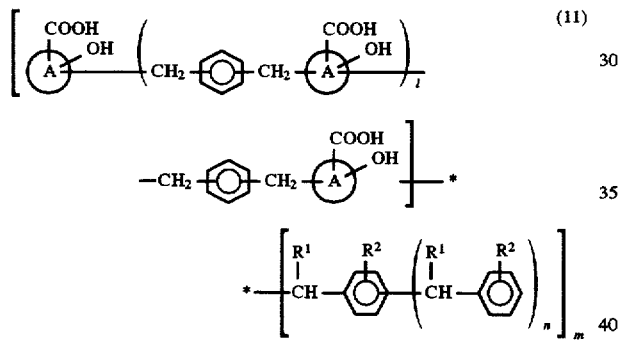

wherein each A group is the same or different and individually represents a substituted or unsubstituted phenylene or naphthylene group, $R^1$ represents a hydrogen atom or a $C_{1-4}$ alkyl group, $R^2$ represents a hydrogen atom, l stands for an integer of 0–100, m stands for an integer of 0–20 and n stands for an integer of 0–3 with the proviso that m stands for an integer other than 0 when all of the A groups represent a substituted phenylene group.

10. A multivalent-metal-modified hydroxycarboxylic acid resin obtained by reacting a hydroxycarboxylic acid with a multivalent metal compound, said hydroxycarboxylic acid resin having a number-average molecular weight of 370–50,000 and being represented by the following formula (1):

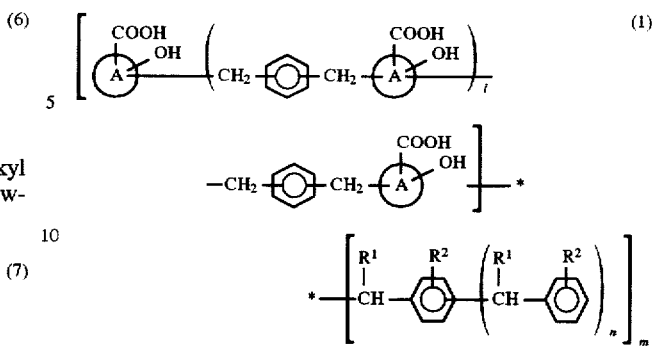

wherein each A group is the same or different and individually represents a substituted or unsubstituted phenylene or naphthylene group, $R^1$ represents a hydrogen atom or a $C_{1-4}$ alkyl group, $R^2$ represents a hydrogen atom, l stands for an integer of 0–100, m stands for an integer of 0–20 and n stands for an integer of 0–3 with the proviso that m stands for an integer other than 0 when all of the A groups represent a substituted or unsubstituted phenylene group.

11. A color-developing sheet comprising a multivalent-metal-modified hydroxycarboxylic acid resin, said hydroxycarboxylic acid resin having a number-average molecular weight of 370–50,000 and having represented by the following formula (1):

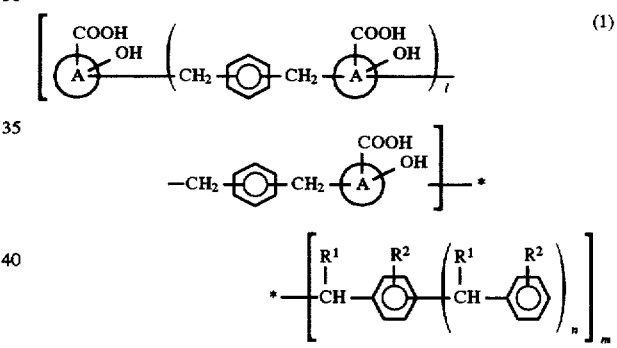

wherein each A group is the same or different and individually represents a substituted or unsubstituted phenylene or naphthylene group, $R^1$ represents a hydrogen atom or a $C_{1-4}$ alkyl group, $R^2$ represents a hydrogen atom, l stands for an integer of 0–100, m stands for an integer of 0–20 and n stands for an integer of 0–3 with the proviso that m stands for an integer other than 0 when all of the A groups represent a substituted or unsubstituted phenylene group.

* * * * *